(12) United States Patent
Miller et al.

(10) Patent No.: US 10,350,068 B2
(45) Date of Patent: Jul. 16, 2019

(54) ACTIVELY-ENGAGEABLE MOVEMENT-RESTRICTION MECHANISM FOR USE WITH AN ANNULOPLASTY STRUCTURE

(71) Applicant: VALTECH CARDIO, LTD., Or Yehuda (IL)

(72) Inventors: Eran Miller, Moshav Beit Elazari (IL); Amir Gross, Moshav Mazor (IL); Oz Cabiri, Hod Hashsaron (IL); Iftah Beinart, Hod Hasharon (IL); Aviram Baum, Tel Aviv (IL)

(73) Assignee: Valtech Cardio, Ltd., Or Yehuda (IL)

( * ) Notice: Subject to any disclaimer, the term of this patent is extended or adjusted under 35 U.S.C. 154(b) by 83 days.

(21) Appl. No.: 15/388,779

(22) Filed: Dec. 22, 2016

(65) Prior Publication Data

US 2017/0100249 A1 Apr. 13, 2017

Related U.S. Application Data

(60) Continuation of application No. 13/740,582, filed on Jan. 14, 2013, now Pat. No. 9,561,104, which is a (Continued)

(51) Int. Cl.
*A61F 2/24* (2006.01)

(52) U.S. Cl.
CPC .......... *A61F 2/2448* (2013.01); *A61F 2/2442* (2013.01); *A61F 2210/0014* (2013.01); (Continued)

(58) Field of Classification Search
CPC ....................................................... A61F 2/24
See application file for complete search history.

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CA 2671966 A1 6/2008
CN 101653365 A 2/2010
(Continued)

OTHER PUBLICATIONS

An Office Action dated Apr. 6, 2017, which issued during the prosecution of U.S. Appl. No. 14/437,062.
(Continued)

*Primary Examiner* — Matthew W Schall
(74) *Attorney, Agent, or Firm* — Thomas C. Richardson

(57) ABSTRACT

Apparatus is provided, including an implant including a flexible longitudinal member extending along a longitudinal length of the implant, and a flexible contracting member extending alongside the longitudinal member and along the longitudinal length of the implant. The contracting member is configured to facilitate reduction of a perimeter of the implant by applying a contracting force to the longitudinal member in response to an application of force to the contracting member. The longitudinal member has first and second ends, and the first end is movable with respect to the second end responsively to the applying of the contracting force to the longitudinal member by the contracting member. The apparatus includes a lock coupled to the longitudinal member. The lock is engageable with the longitudinal member to restrict movement of the longitudinal member.

18 Claims, 6 Drawing Sheets

Related U.S. Application Data division of application No. 12/706,868, filed on Feb. 17, 2010, now Pat. No. 8,353,956.

(60) Provisional application No. 61/207,908, filed on Feb. 17, 2009.

(52) U.S. Cl.
CPC ............. *A61F 2250/0004* (2013.01); *A61F 2250/0007* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,961,738 A | 10/1990 | Mackin |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,450,860 A | 9/1995 | O'Connor |
| 5,474,518 A | 12/1995 | Ferrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,669,919 A | 9/1997 | Sanders et al. |
| 5,674,279 A | 10/1997 | Wright et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,401 A | 6/2000 | Gardiner et al. |
| 6,074,417 A | 6/2000 | Peredo |
| 6,102,945 A | 8/2000 | Campbell |
| 6,106,550 A | 8/2000 | Magovern et al. |
| 6,110,200 A | 8/2000 | Hinnenkamp |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,332,893 B1 | 12/2001 | Mortier et al. |
| 6,355,030 B1 | 3/2002 | Aldrich et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |

(56) References Cited

U.S. PATENT DOCUMENTS

| | | |
|---|---|---|
| 6,893,459 B1 | 5/2005 | Macoviak |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,176,550 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,297,150 B2 | 11/2007 | Cartledge et al. |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Gringo et al. |
| 7,955,377 B2 | 6/2011 | Melsheimer |
| 7,988,725 B2 | 8/2011 | Gross et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,800 B2 | 2/2012 | McCarthy et al. |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,226,711 B2 | 7/2012 | Mortier et al. |
| 8,231,671 B2 | 7/2012 | Kim |
| 8,241,351 B2 | 8/2012 | Cabiri |
| 8,252,050 B2 | 8/2012 | Maisano et al. |
| 8,262,725 B2 | 9/2012 | Subramanian |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,430,926 B2 | 4/2013 | Kirson |

(56) References Cited

U.S. PATENT DOCUMENTS

| | | |
|---|---|---|
| 8,449,599 B2 | 5/2013 | Chau et al. |
| 8,454,686 B2 | 6/2013 | Alkhatib |
| 8,460,370 B2 | 6/2013 | Zakay et al. |
| 8,460,371 B2 | 6/2013 | Hlavka et al. |
| 8,475,491 B2 | 7/2013 | Milo |
| 8,480,732 B2 | 7/2013 | Subramanian |
| 8,500,800 B2 | 8/2013 | Maisano et al. |
| 8,518,107 B2 | 8/2013 | Tsukashima et al. |
| 8,523,881 B2 | 9/2013 | Cabiri et al. |
| 8,523,940 B2 | 9/2013 | Richardson et al. |
| 8,545,553 B2 | 10/2013 | Zipory et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,690,939 B2 | 4/2014 | Miller et al. |
| 8,715,342 B2 | 5/2014 | Zipory et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,808,371 B2 | 8/2014 | Cartledge |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,042 B2 | 1/2015 | Miller et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,226,825 B2 | 1/2016 | Starksen et al. |
| 9,241,702 B2 | 1/2016 | Maisano et al. |
| 9,265,608 B2 | 2/2016 | Miller et al. |
| 9,326,857 B2 | 5/2016 | Cartledge et al. |
| 9,351,830 B2 | 5/2016 | Gross et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 2001/0021874 A1 | 9/2001 | Carpentier et al. |
| 2001/0044656 A1 | 11/2001 | Williamson, IV et al. |
| 2002/0022862 A1 | 2/2002 | Grafton et al. |
| 2002/0029080 A1 | 3/2002 | Mortier et al. |
| 2002/0042621 A1 | 4/2002 | Liddicoat et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0133180 A1 | 9/2002 | Ryan et al. |
| 2002/0151916 A1 | 10/2002 | Muramatsu et al. |
| 2002/0151961 A1 | 10/2002 | Lashinski et al. |
| 2002/0151970 A1 | 10/2002 | Garrison et al. |
| 2002/0169358 A1 | 11/2002 | Mortier et al. |
| 2002/0173841 A1 | 11/2002 | Ortiz et al. |
| 2002/0177904 A1 | 11/2002 | Huxel et al. |
| 2002/0188301 A1 | 12/2002 | Dallara et al. |
| 2002/0198586 A1 | 12/2002 | Inoue |
| 2003/0018358 A1 | 1/2003 | Saadat |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083742 A1 | 5/2003 | Spence et al. |
| 2003/0100943 A1 | 5/2003 | Bolduc |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0130731 A1 | 7/2003 | Vidlund et al. |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0191528 A1 | 10/2003 | Quijano et al. |
| 2003/0199974 A1 | 10/2003 | Lee et al. |
| 2003/0204195 A1 | 10/2003 | Keane et al. |
| 2003/0229350 A1 | 12/2003 | Kay |
| 2003/0229395 A1 | 12/2003 | Cox |
| 2003/0233142 A1 | 12/2003 | Morales et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0049207 A1 | 3/2004 | Goldfarb et al. |
| 2004/0059413 A1 | 3/2004 | Argento |
| 2004/0092962 A1 | 5/2004 | Thornton et al. |
| 2004/0122448 A1 | 6/2004 | Levine |
| 2004/0122514 A1 | 6/2004 | Fogarty et al. |
| 2004/0127982 A1 | 7/2004 | Machold et al. |
| 2004/0127983 A1 | 7/2004 | Mortier et al. |
| 2004/0133220 A1 | 7/2004 | Lashinski et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153146 A1 | 8/2004 | Lashinski et al. |
| 2004/0172046 A1 | 9/2004 | Hlavka et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0236419 A1 | 11/2004 | Milo |
| 2004/0243227 A1 | 12/2004 | Starksen et al. |

(56) References Cited

U.S. PATENT DOCUMENTS

| | | |
|---|---|---|
| 2004/0249453 A1 | 12/2004 | Cartledge et al. |
| 2004/0260317 A1 | 12/2004 | Bloom et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0085903 A1 | 4/2005 | Lau |
| 2005/0090827 A1 | 4/2005 | Gedebou |
| 2005/0096740 A1 | 5/2005 | Langberg et al. |
| 2005/0107812 A1 | 5/2005 | Starksen et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187613 A1 | 8/2005 | Bolduc et al. |
| 2005/0192596 A1 | 9/2005 | Jugenheimer et al. |
| 2005/0197696 A1 | 9/2005 | Gomez Duran |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0222678 A1 | 10/2005 | Lashinski et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288776 A1 | 12/2005 | Shaoulian et al. |
| 2005/0288778 A1 | 12/2005 | Shaoulian et al. |
| 2005/0288781 A1 | 12/2005 | Moaddeb et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025855 A1 | 2/2006 | Lashinski et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0052868 A1 | 3/2006 | Mortier et al. |
| 2006/0058871 A1 | 3/2006 | Zakay et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | BAnbury et al. |
| 2007/0001627 A1 | 1/2007 | Lin et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0038221 A1 | 2/2007 | Fine et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0233239 A1 | 10/2007 | Navia et al. |
| 2007/0239208 A1 | 10/2007 | Crawford |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Huaser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0125861 A1 | 5/2008 | Webler et al. |
| 2008/0140116 A1 | 6/2008 | Bonutti |
| 2008/0167714 A1 | 7/2008 | St. Goar et al. |
| 2008/0177382 A1 | 7/2008 | Hyde et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0243245 A1 | 10/2008 | Thambar et al. |
| 2008/0262480 A1 | 10/2008 | Stahler et al. |
| 2008/0262609 A1 | 10/2008 | Gross et al. |

(56) References Cited

U.S. PATENT DOCUMENTS

| | | |
|---|---|---|
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043153 A1 | 2/2009 | Zollinger et al. |
| 2009/0043381 A1 | 2/2009 | Macoviak et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0149872 A1 | 6/2009 | Gross et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0177277 A1 | 7/2009 | Milo |
| 2009/0222083 A1 | 9/2009 | Nguyen et al. |
| 2009/0248148 A1 | 10/2009 | Shaolian et al. |
| 2009/0254103 A1 | 10/2009 | Deutsch |
| 2009/0259307 A1 | 10/2009 | Gross et al. |
| 2009/0264994 A1 | 10/2009 | Saadat |
| 2009/0264995 A1 | 10/2009 | Subramanian |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023117 A1 | 1/2010 | Yoganathan et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049313 A1 | 2/2010 | Alon et al. |
| 2010/0063542 A1 | 3/2010 | van der Burg et al. |
| 2010/0063550 A1 | 3/2010 | Felix et al. |
| 2010/0063586 A1 | 3/2010 | Hasenkam et al. |
| 2010/0076499 A1 | 3/2010 | McNamara et al. |
| 2010/0094248 A1 | 4/2010 | Nguyen et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0198347 A1 | 8/2010 | Zakay et al. |
| 2010/0211166 A1 | 8/2010 | Miller et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0305475 A1 | 12/2010 | Hinchcliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0166649 A1 | 7/2011 | Gross et al. |
| 2011/0184510 A1 | 7/2011 | Maisano et al. |
| 2011/0190879 A1 | 8/2011 | Bobo et al. |
| 2011/0202130 A1 | 8/2011 | Cartledge et al. |
| 2011/0208283 A1 | 8/2011 | Rust |
| 2011/0224785 A1 | 9/2011 | Hacohen |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0257728 A1 | 10/2011 | Kuehn |
| 2011/0264208 A1 | 10/2011 | Duffy et al. |
| 2011/0276062 A1 | 11/2011 | Bolduc |
| 2011/0282361 A1 | 11/2011 | Miller et al. |
| 2011/0288435 A1 | 11/2011 | Christy et al. |
| 2011/0288635 A1 | 11/2011 | Miller et al. |
| 2011/0301498 A1 | 12/2011 | Maenhout et al. |
| 2011/0301698 A1 | 12/2011 | Miller et al. |
| 2012/0022557 A1 | 1/2012 | Cabiri et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035712 A1 | 2/2012 | Maisano et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095552 A1 | 4/2012 | Spence et al. |
| 2012/0109155 A1 | 5/2012 | Robinson et al. |
| 2012/0123531 A1 | 5/2012 | Tsukashima et al. |
| 2012/0136436 A1 | 5/2012 | Cabiri et al. |
| 2012/0143323 A1 | 6/2012 | Hasenkam et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191182 A1 | 7/2012 | Hauser et al. |
| 2012/0197388 A1 | 8/2012 | Khairkhahan et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller et al. |
| 2012/0296349 A1 | 11/2012 | Smith et al. |
| 2012/0296417 A1 | 11/2012 | Hill et al. |
| 2012/0296419 A1 | 11/2012 | Richardson et al. |
| 2012/0310330 A1 | 12/2012 | Buchbinder et al. |
| 2012/0323313 A1 | 12/2012 | Seguin |
| 2012/0330410 A1 | 12/2012 | Hammer et al. |
| 2012/0330411 A1 | 12/2012 | Gross et al. |
| 2013/0023758 A1 | 1/2013 | Fabro |
| 2013/0030522 A1 | 1/2013 | Rowe et al. |
| 2013/0035759 A1 | 2/2013 | Gross et al. |
| 2013/0046373 A1 | 2/2013 | Cartledge et al. |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096672 A1 | 4/2013 | Reich et al. |
| 2013/0096673 A1 | 4/2013 | Hill et al. |
| 2013/0116776 A1 | 5/2013 | Gross et al. |

(56) References Cited

U.S. PATENT DOCUMENTS

| | | |
|---|---|---|
| 2013/0116780 A1 | 5/2013 | Miller et al. |
| 2013/0123910 A1 | 5/2013 | Cartledge et al. |
| 2013/0131791 A1 | 5/2013 | Hlavka et al. |
| 2013/0131792 A1 | 5/2013 | Miller et al. |
| 2013/0166017 A1 | 6/2013 | Cartledge et al. |
| 2013/0172992 A1 | 7/2013 | Gross et al. |
| 2013/0190863 A1 | 7/2013 | Call et al. |
| 2013/0190866 A1 | 7/2013 | Zipory et al. |
| 2013/0197632 A1 | 8/2013 | Kovach et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0325118 A1 | 12/2013 | Cartledge |
| 2014/0018914 A1 | 1/2014 | Zipory et al. |
| 2014/0088368 A1 | 3/2014 | Park |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0148898 A1 | 5/2014 | Gross et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0222137 A1 | 8/2014 | Miller et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0257475 A1 | 9/2014 | Gross et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0324164 A1 | 10/2014 | Gross et al. |
| 2014/0343668 A1 | 11/2014 | Zipory et al. |
| 2014/0379006 A1 | 12/2014 | Sutherland et al. |
| 2015/0012087 A1 | 1/2015 | Miller et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0105855 A1 | 4/2015 | Cabiri et al. |
| 2015/0112432 A1 | 4/2015 | Reich et al. |
| 2015/0127097 A1 | 5/2015 | Neumann et al. |
| 2015/0182336 A1 | 7/2015 | Zipory et al. |
| 2015/0230924 A1 | 8/2015 | Miller et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0297212 A1 | 10/2015 | Reich et al. |
| 2015/0351906 A1 | 12/2015 | Hammer et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0324633 A1 | 11/2016 | Gross et al. |
| 2016/0361168 A1 | 12/2016 | Gross et al. |
| 2016/0361169 A1 | 12/2016 | Gross et al. |
| 2017/0000609 A1 | 1/2017 | Gross et al. |

FOREIGN PATENT DOCUMENTS

| | | |
|---|---|---|
| EP | 0611561 A1 | 8/1994 |
| EP | 0614342 A1 | 9/1994 |
| EP | 0871417 B1 | 10/1998 |
| EP | 0954257 B1 | 11/1999 |
| EP | 1006905 A1 | 6/2000 |
| EP | 1034753 B1 | 9/2000 |
| EP | 1258232 B1 | 11/2002 |
| EP | 1258437 A1 | 11/2002 |
| EP | 1266641 B1 | 12/2002 |
| EP | 1418865 B1 | 5/2004 |
| EP | 1420723 B1 | 5/2004 |
| EP | 1450733 B1 | 9/2004 |
| EP | 1465555 B1 | 10/2004 |
| EP | 1531762 B1 | 5/2005 |
| EP | 1562522 B1 | 8/2005 |
| EP | 1861045 B1 | 12/2007 |
| EP | 1903991 B1 | 4/2008 |
| EP | 1990014 A2 | 11/2008 |
| EP | 2119399 A1 | 11/2009 |
| IL | 223448 | 12/2012 |
| WO | 92/05093 A1 | 4/1992 |
| WO | 93/10714 A1 | 6/1993 |
| WO | 93/15690 A2 | 8/1993 |
| WO | 96/39963 A1 | 12/1996 |
| WO | 96/40344 A1 | 12/1996 |
| WO | 97/01369 A1 | 1/1997 |
| WO | 98/46149 A1 | 10/1998 |
| WO | 99/30647 A1 | 6/1999 |
| WO | 99/33414 A1 | 7/1999 |
| WO | 99/63907 A1 | 12/1999 |
| WO | 99/63910 A1 | 12/1999 |
| WO | 00/09048 A1 | 2/2000 |
| WO | 00/22981 A1 | 4/2000 |
| WO | 01/26586 A1 | 4/2001 |
| WO | 01/56457 A1 | 8/2001 |
| WO | 01/87191 A1 | 11/2001 |
| WO | 02/085250 A2 | 10/2002 |
| WO | 02/085251 A1 | 10/2002 |
| WO | 02/085252 A1 | 10/2002 |
| WO | 03/028558 A2 | 4/2003 |
| WO | 03/047467 A1 | 6/2003 |
| WO | 03049647 A1 | 6/2003 |
| WO | 03/105667 A2 | 12/2003 |
| WO | 2004/012583 A2 | 2/2004 |
| WO | 2004/019816 A2 | 3/2004 |
| WO | 2004/019826 A1 | 3/2004 |
| WO | 2004/103434 A2 | 12/2004 |
| WO | 2005/021063 A2 | 3/2005 |
| WO | 2005/046488 A2 | 5/2005 |
| WO | 2005/062931 A2 | 7/2005 |
| WO | 2006/012013 A2 | 2/2006 |
| WO | 2006/012038 A2 | 2/2006 |
| WO | 2006/086434 A1 | 8/2006 |
| WO | 2006/097931 A2 | 9/2006 |
| WO | 2006/105084 A2 | 10/2006 |
| WO | 2006/116558 A2 | 11/2006 |
| WO | 2007/011799 A1 | 1/2007 |
| WO | 2007/080595 A2 | 7/2007 |
| WO | 2007/121314 A2 | 10/2007 |
| WO | 2007/136783 A2 | 11/2007 |
| WO | 2007/136981 A2 | 11/2007 |
| WO | 2008/014144 A2 | 1/2008 |
| WO | 2008/031103 A2 | 3/2008 |
| WO | 2008/068756 A2 | 6/2008 |
| WO | 2009/130631 A2 | 10/2009 |
| WO | 2010/000454 A1 | 1/2010 |
| WO | 2010/004546 A1 | 1/2010 |
| WO | 2010/006905 A1 | 1/2010 |
| WO | 2010/044851 A1 | 4/2010 |
| WO | 2010/065274 A1 | 6/2010 |
| WO | 2010/073246 A2 | 7/2010 |
| WO | 2010/085649 A1 | 7/2010 |
| WO | 2010/128502 A1 | 11/2010 |

(56) References Cited

FOREIGN PATENT DOCUMENTS

| | | |
|---|---|---|
| WO | 2010/128503 A2 | 11/2010 |
| WO | 2010/150178 A2 | 12/2010 |
| WO | 2011/051942 A1 | 5/2011 |
| WO | 2011/067770 A1 | 6/2011 |
| WO | 2011/089401 A1 | 7/2011 |
| WO | 2011/089601 A1 | 7/2011 |
| WO | 2011/111047 A2 | 9/2011 |
| WO | 2011/148374 A2 | 12/2011 |
| WO | 2011/154942 A2 | 12/2011 |
| WO | 2012/011108 A2 | 1/2012 |
| WO | 2012/014201 A2 | 2/2012 |
| WO | 2012/068541 A2 | 5/2012 |
| WO | 2012/106346 A1 | 8/2012 |
| WO | 2012/176195 A2 | 12/2012 |
| WO | 2013/021374 A2 | 2/2013 |
| WO | 2013/021375 A2 | 2/2013 |
| WO | 2013/069019 A2 | 5/2013 |
| WO | 2013/078497 A1 | 6/2013 |
| WO | 2013/088327 A1 | 6/2013 |
| WO | 2014/064695 A2 | 5/2014 |
| WO | 2014/064964 A1 | 5/2014 |
| WO | 2014/076696 A1 | 5/2014 |
| WO | 2014/087402 A1 | 6/2014 |
| WO | 2014/108903 A1 | 7/2014 |
| WO | 2014/115149 A2 | 7/2014 |
| WO | 2014/195786 A2 | 12/2014 |
| WO | 2015/059699 A2 | 4/2015 |
| WO | 2015/193728 A2 | 12/2015 |
| WO | 2016/059639 A1 | 4/2016 |
| WO | 2016/087934 A1 | 6/2016 |
| WO | 2016/174669 A1 | 11/2016 |

OTHER PUBLICATIONS

Notice of Allowance dated Apr. 13, 2017, which issued during the prosecution of U.S. Appl. No. 14/650,114.
An Office Action dated Mar. 24, 2017, which issued during the prosecution of U.S. Appl. No. 14/273,155.
Shikhar Agarwal, et al; "Interventional Cardiology Perspective of Functional Tricuspid Regurgitation", Circ Cardiovasc Interv 2009;2;2;565-573 (2009).
A Ahmadi, et al; "Hemodynamic Changes Following Experimental Production and Correction of Acute Mitral Regurgitation with an Adustable Ring Prosthesis", The Thoracic and Cardiovascular Surgeon 36.06 (1988): 313-319.
Ali Ahmadi, et al; "Percutaneously Adjustable Pulmonary Artery Band", The Annals of Thoracic Surgery 60 (1995): S520-S522.
Ottavio Alfieri, et al; "An Effective Technique to Correct Anterior Mitral Leaflet Prolapse", J. Card 14(6): 468-470 (1999).
Ottavio Alfieri, et al "The double-orifice technique in mitral valve repair: A simple solution for complex problems", Journal of Thoracic Cardiovascular Surgery 122: 674-681 (2001).
Ottavio Alfieri, "The Edge-To-Edge Repair of the Mitral Valve", (Abstract) 6th Annual NewEra Cardiac Care: Innovation & Technology, Heart Surgery Forum pp. 103 (2000).
Ottavio Alfieri, et al; "Novel suture device for beating-heart mitral leaflet approxiamation", Ann. Thorac. Surg. 2002, 74:1488-1493.
Amplatzer Cardiac Plug Brochure (English pages), AGA Medical Corporation (Plymouth, MN) Copyright 2008-2010, downloaded Jan. 11, 2011.
AMPLATZER® Cribrigorm Occluder. A patient guide to Percutaneous, Transcatheter, Atrial Septal Defect Closure, AGA Medical Corporation. Apr. 2008, 19 pages.
AMPLATZER® Septal Occluder; "A Patient's Guide to the Non-Surgical Closure of the Atrial Septal Defect Using the Amplatzer Septal Occluder System", AGA Medicla Corporation, Apr. 2008, 19 pages.
Rentato S Assad; "Adjustable Pulmonary Artery Banding", (2014); INTECH-Cardiac Surgery—A commitment to Science, Technology and Creativity, 32 pages.
Jennifer Brennan; 510(k) Summary of Safety and Effectiveness, Jan. 2008; 5 pages.
S. Dabritz, et al; Experience With an Adjustable Pulmonary Artery Banding Device in Two Cases: Initial Success-Midterm Failure: The Thoracic and Cardiovascular Surgeon 47.01 (1999): 51-52.
Nicholas C. Dang, et al; "Simplified Placement of Multiple Artificial Mitral Valve Chords", The Heart Surgery Forum #2005-1005, 8 (3) Epub Apr. 2005; 3 pages.
DICTIONARY.com definition of "lock", Jul. 29, 2013 4 pages.
Robert S. Dieter; "Percutaneous valve repair: Update on mitral regurtitation and endovascular approaches to the mitral valve", Applications in Imaging, Cardiac Interventions, Supported by an educationjal grant from Amersham Health pp. 11-14 (2003).
Francesco Maisano, et al; "The double-orifice technique as a standardized approach to treat mitral regurgitation due to severe myxomatous disease: surgical technique", European Journal of Cardio-thoracic Surgery 17 (2000) 201-205.
Daniel S. Elliott, et al; "An Implantable Mechanical Urinary Sphincter: A New Nonhydraulic Design Concept", Urology 52.6 (1998): 1151-1154.
Orvar Swenson; "An Experimental Implantable Urinary Sphincter", Invest Urol. Sep. 1976; 14)2): 100-3.
Frank Langer, et al; "Ring+String Successful Repair Technique for Ischemic Mitral Regurgitation With Severe Leaflet Tethering", The Department of Thoracic Cardiovascular Surgery, Hamburg, Germany, Nov. 2008 10 pages.
Frank Langer, et al; "Ring plus String: Papillary muscle repositioning as an adjunctive repair technique for ischemic mitral regurgitation" The Journal of Thoracic Cardiovascular Surgery, vol. 133, No. 1, Jan. 2007.
F. Maisano, et al; "The edge-to-edge technique: a simplified method to correct mitral insufficiency", The European Association for Cardio-Thoracic Surgery 14th Annual Meeting Oct. 7-11, Book of Process. (2000).
John A. Odell, et al; "Early Results of a Simplified Method of Mitral Valve Annuloplasty", Circulation 92:150-154 (1995).
S. O'Reilly et al; "Heart Valve Surgery Pushes the Envelope", Medtech Insight 8(3): 73, 99-108 (2006).
Sang C. Park, et al; "A percutaneously adjustable device for banding of the pulmonary trunk", International Journal of Cardiology 9.4 (1985): 477-484.
C. Paul Swain, et al; "An endoscopically deliverable tissue-transfixing device for securing biosensors in the gastrointestinal tract", Gastrointestinal Endoscopy 40(6): 730-734 (1994).
Orvar Swenson, et al; "An Improved Mechanical Device for Control of Urinary Incontinence", Investigative Urology, 15(5), pp. 389-391; 1978.
Orvar Swenson; "Internal Device for Control of Urinary Incontinence", Journal of Pediatric Surgery 7.5 (1972): 542-545.
Abdul J. Tajik, et al; "Two-Dimensional Real-Time Ultrasonic Imaging of the Heart and Great Vessels", Mayo Clinic Proceedings, vol. 53, May 1978, 271-303.
Supplementary European Search Report dated Apr. 29, 2015; EP14200202.
Supplementary European Search Report dated Jan. 17, 2014; EP10772090.6.
Supplementary European Search Report dated Jan. 20, 2015; EP12803037.6.
Supplementary European Search Report dated Jan. 21, 2014; EP11786226.8.
Supplementary European Search Report dated Feb. 1, 2011; EP07849540.
Supplementary European Search Report dated Mar. 23, 2015; EP11792047.0.
Supplementary European Search Report dated Apr. 10, 2013: EP10772091.4.
Supplementary European Search Report dated Jun. 24, 2016; EP12847363.
Supplementary European Search Report dated Jul. 8, 2016; EP13849843.1.
Supplementary European Search Report dated Jul. 15, 2016; EP13849947.0.

(56) References Cited

OTHER PUBLICATIONS

Supplementary European Search Report dated Aug. 4, 2014; EP11811934.6.
Supplementary European Search Report dated Sep. 25, 2015; EP09794095.1.
Supplementary European Search Report dated Oct. 23, 2014; EP1086224.7.
Supplementary European Search Report dated Dec. 4, 2012; EP09834225.6.
Supplementary European Search Report dated Dec. 23, 2014; EP10834311.
EPO Office Action dated Dec. 13, 2016; EP11786226.8.
EPO Office Action dated Mar. 3, 2017; EP11792047.0.
EPO Communication dated Mar. 23, 2015; EP09834225.6.
EPO Communication dated Jun. 11, 2015; EP11811934.6.
EPO Communication dated Sep. 28, 2011; EP09834225.6.
EPO Communication dated Oct. 19, 2012; EP 11792047.0.
EPO Communication dated Nov. 4, 2015; EP10772091.4.
EPO Communication dated Nov. 16, 2015; EP10826224.7.
EPO Communication dated Dec. 27, 2012; EP11792047.0.
Invite to pay fees; dated Jan. 31, 2014; PCT/IL13/50860.
Invite to pay fees; dated Jan. 31, 2014; PCT/IL13/50861.
Invite to pay fees; dated Aug. 18, 2016; PCT/IL2016/050433.
Chinese Notice of Allowance dated Aug. 7, 2015; Appln. No. 200980157331.3.
First Chinese Office Action dated Dec. 12, 2013; Appln. No. 200980157331.3.
First Chinese Office Action dated Apr. 23, 2014; Appln. No. 201080059948.4.
First Chinese Office Action dated Jan. 25, 2017; Appln. No. 201510681407.X.
Second Chinese Office Action dated Jul. 25, 2014; Appln. No. 200980157331.3.
Third Chinese Office Action dated Jul. 17, 2015; Appln. No. 201080059948.
Japanese Office Action dated Oct. 23, 2012; Appln. No. 2009-539871.
United Kingdom Office Action dated Dec. 20, 2016; Appln. No. 1611910.9.
Israel Office Action dated May 31, 2012; 209946 (English translation of the relevant part only).
Israel Office Action dated Nov. 24, 2015; 223448 (English translation of the relevant part only).
Israel Office Action dated Sep. 15, 2016; 243837 (English translation of the relevant part only).
IPRP dated Sep. 18, 2007; PCT/IL2006/000342.
IPRP dated Jun. 10, 2009; PCT/IL2007/001503.
IPRP dated Dec. 18, 2010; PCT/IL2009/000593.
IPRP dated Jun. 29, 2011; PCT/IL2009/001209.
IPRP dated Nov. 9, 2011; PCT/IL2010/000357.
IPRP dated Nov. 9, 2011; PCT/IL2010/000358.
IPRP dated May 1, 2012; PCT/IL2010/000890.
IPRP dated Jun. 5, 2012; PCT/IL2010/001024.
IPRP dated Nov. 27, 2012; PCT/IL2011/000404.
IPRP dated Feb. 4, 2014; PCT/IL2011/000446.
IPRP dated Jan. 29, 2013; PCT/IL2011/000600.
IPRP dated Dec. 23, 2013; PCT/IL2012000250.
IPRP dated Dec. 23, 2014; PCT/IL2012/050451.
IPRP dated Apr. 28, 2015; PCT/IL2013/050860.
IPRP dated Apr. 28, 2015; PCT/IL2013/050861.
IPRP dated Jun. 9, 2015; PCT/IL2013/050992.
IPRP dated Apr. 26, 2016; PCT/IL2014/050914.
ISR dated May 11, 2019; PCT/IL2011/000064.
ISR & WO dated Jun. 10, 2010; PCT/IL09/01209.
ISR & WO dated Aug. 17, 2010; PCT/IL10/00357.
ISR & WO dated Feb. 10, 2011; PCT/IL10/00890.
ISR & WO dated Sep. 12, 2008; PCT/IL2007/01503.
ISR & WO dated Feb. 22, 2013; PCT/IL2010/504451.
ISR & WO dated Nov. 23, 2011; PCT/IL2011/00446.
ISR & WO dated May 30, 2007; PCT/IL2006/000342.
ISR & WO dated Sep. 8, 2009; PCT/IL2009/000593.
ISR & WO dated Nov. 8, 2010; PCT/IL2010/000358.
ISR & WO dated Mar. 30, 2011; PCT/IL2010/001024.
ISR & WO dated Nov. 14, 2011; PCT/IL2011/000404.
ISR & WO dated Feb. 2, 2012; PCT/IL2011/000600.
ISR & WO dated Dec. 6, 2012; PCT/IL2012/000250.
ISR & WO dated Apr. 9, 2014; PCT/IL2013/050860.
ISR & WO dated Apr. 15, 2014; PCT/IL2013/050861.
ISR & WO dated Mar. 21, 2014; PCT/IL2013/050992.
ISR & WO dated May 28, 2014; PCT/IL2014/050027.
ISR & WO dated May 12, 2015; PCT/IL2014/050914.
ISR & WO dated Oct. 27, 2015; PCT/IL2015/050792.
ISR & WO dated Jan. 25, 2016; PCT/IL2015/051027.
ISR & WO dated Oct. 17, 2016; PCT/IL2016/050433.
U.S. Appl. No. 60/662,616, filed Mar. 17, 2005.
U.S. Appl. No. 60/700,542, filed Jul. 18, 2005.
U.S. Appl. No. 60/873,075, filed Dec. 5, 2006.
U.S. Appl. No. 60/902,146, filed Feb. 16, 2007.
U.S. Appl. No. 61/001,013, filed Oct. 29, 2007.
U.S. Appl. No. 61/132,295, filed Jun. 16, 2008.
U.S. Appl. No. 61/207,908, filed Feb. 17, 2009.
U.S. Appl. No. 61/265,936, filed Dec. 2, 2009.
U.S. Appl. No. 61/283,445, filed Dec. 2, 2009.
U.S. Appl. No. 61/555,570, filed Nov. 4, 2011.
U.S. Appl. No. 61/557,082, filed Nov. 8, 2011.
U.S. Appl. No. 61/717,303, filed Oct. 23, 2012.
U.S. Appl. No. 61/733,979, filed Dec. 6, 2012.
U.S. Appl. No. 61/745,848, filed Dec. 6, 2012.
U.S. Appl. No. 61/820,979, filed May 8, 2013.
USPTO AA dated Feb. 4, 2014; U.S. Appl. No. 13/167,476.
USPTO AA dated Sep. 6, 2012; U.S. Appl. No. 12/548,991.
USPTO Comm dated Dec. 24, 2014; U.S. Appl. No. 12/795,026.
USPTO Corrected NOA dated Jan. 7, 2016; U.S. Appl. No. 13/319,007.
USPTO Corrected NOA dated Mar. 6, 2014; U.S. Appl. No. 12/437,103.
USPTO Corrected NOA dated May 22, 2015; U.S. Appl. No. 13/749,153.
USPTO Corrected NOA dated Jul. 24, 2015; U.S. Appl. No. 13/707,013.
USPTO Corrected NOA dated Aug. 3, 2015; U.S. Appl. No. 13/749,153.
USPTO Corrected NOA dated Sep. 14, 2015; U.S. Appl. No. 13/707,013.
USPTO Corrected NOA dated Oct. 20, 2015; U.S. Appl. No. 12/996,954.
USPTO Corrected NOA dated Dec. 21, 2016; U.S. Appl. No. 14/246,417.
Filing of Amendment, Extension with USPTO dated Apr. 11, 2012; U.S. Appl. No. 12/563,952.
Filing of Amendment and Terminal Disclaimer with USPTO dated Jun. 27, 2012; U.S. Appl. No. 12/548,991.
USPTO FOA dated Jan. 5, 2016; U.S. Appl. No. 14/084,426.
USPTO FOA dated Jan. 6, 2016; U.S. Appl. No. 14/128,756.
USPTO FOA dated Feb. 2, 2017; U.S. Appl. No. 14/209,171.
USPTO FOA dated Feb. 3, 2014; U.S. Appl. No. 12/689,693.
USPTO FOA dated Mar. 27, 2013; U.S. Appl. No. 12/843,412.
USPTO FOA dated Mar. 29, 2011; U.S. Appl. No. 12/341,960.
USPTO FOA dated Apr. 2, 2015; U.S. Appl. No. 14/027,934.
USPTO FOA dated May 4, 2016; U.S. Appl. No. 14/589,100.
USPTO FOA dated May 30, 2012; U.S. Appl. No. 12/706,868.
USPTO FOA dated Jun. 11, 2014; U.S. Appl. No. 14/027,934.
USPTO FOA dated Jun. 13, 2012; U.S. Appl. No. 12/437,103.
USPTO FOA dated Jun. 13, 2014; U.S. Appl. No. 13/141,606.
USPTO FOA dated Jun. 18, 2015; U.S. Appl. No. 13/319,030.
USPTO FOA dated Jul. 18, 2013; U.S. Appl. No. 13/044,694.
USPTO FOA dated Jul. 20, 2016; U.S. Appl. No. 14/246,417.
USPTO FOA dated Aug. 5, 2010; U.S. Appl. No. 11/950,930.
USPTO FOA dated Aug. 6, 2012; U.S. Appl. No. 12/548,991.
USPTO FOA dated Aug. 15, 2013; U.S. Appl. No. 12/795,192.
USPTO FOA dated Aug. 23, 2013; U.S. Appl. No. 13/167,444.
USPTO FOA dated Sep. 6, 2016; U.S. Appl. No. 14/141,228.
USPTO FOA dated Oct. 2, 2013; U.S. Appl. No. 13/167,492.
USPTO FOA dated Oct. 9, 2013; U.S. Appl. No. 12/996,954.

(56) References Cited

OTHER PUBLICATIONS

USPTO FOA dated Oct. 22, 2013; U.S. Appl. No. 12/926,673.
USPTO FOA dated Nov. 5, 2012; U.S. Appl. No. 12/795,026.
USPTO FOA dated Nov. 21, 2013; U.S. Appl. No. 13/167,476.
USPTO FOA dated Nov. 30, 2012; U.S. Appl. No. 12/689,635.
USPTO FOA dated Dec. 21, 2012; U.S. Appl. No. 11/908,906.
USPTO FOA dated Dec. 27, 2013; U.S. Appl. No. 12/785,717.
USPTO Interview Summary dated Apr. 4, 2012; U.S. Appl. No. 12/563,952.
USPTO Interview Summary dated Jul. 27, 2011; U.S. Appl. No. 12/341,960.
USPTO NFOA dated Jan. 4, 2016; U.S. Appl. No. 14/589,100.
USPTO NFOA dated Jan. 5, 2016; U.S. Appl. No. 14/027,934.
USPTO NFOA dated Jan. 17, 2013; U.S. Appl. No. 12/795,192.
USPTO NFOA dated Jan. 17, 2013; U.S. Appl. No. 13/167,444.
USPTO NFOA dated Jan. 20, 2017; U.S. Appl. No. 14/650,114.
USPTO NFOA dated Jan. 27, 2012; U.S. Appl. No. 12/548,991.
USPTO NFOA dated Feb. 10, 2017; U.S. Appl. No. 14/990,172.
USPTO NFOA dated Feb. 12, 2013; U.S. Appl. No. 12/926,673.
USPTO NFOA dated Feb. 14, 2013; U.S. Appl. No. 13/167,492.
USPTO NFOA dated Feb. 17, 2010; U.S. Appl. No. 11/950,930.
USPTO NFOA dated Feb. 27, 2017; U.S. Appl. No. 15/249,957.
USPTO NFOA dated Mar. 9, 2012; U.S. Appl. No. 12/689,635.
USPTO NFOA dated Mar. 16, 2015; U.S. Appl. No. 14/084,426.
USPTO NFOA dated Mar. 23, 2015; U.S. Appl. No. 13/707,013.
USPTO NFOA dated Mar. 24, 2015; U.S. Appl. No. 12/996,954.
USPTO NFOA dated Mar. 24, 2015; U.S. Appl. No. 14/486,226.
USPTO NFOA dated Apr. 1, 2013; U.S. Appl. No. 13/167,476.
USPTO NFOA dated Apr. 2, 2013; U.S. Appl. No. 12/785,717.
USPTO NFOA dated Apr. 6, 2010; U.S. Appl. No. 12/484,512.
USPTO NFOA dated Apr. 7, 2016; U.S. Appl. No. 14/242,151.
USPTO NFOA dated Apr. 8, 2016; U.S. Appl. No. 14/141,228.
USPTO NFOA dated May 3, 2016; U.S. Appl. No. 13/319,030.
USPTO NFOA dated May 6, 2013; U.S. Appl. No. 12/689,693.
USPTO NFOA dated May 10, 2012; U.S. Appl. No. 12/795,026.
USPTO NFOA dated May 11, 2016; U.S. Appl. No. 14/128,756.
USPTO NFOA dated May 23, 2016; U.S. Appl. No. 14/209,171.
USPTO NFOA dated Jun. 4, 2014; U.S. Appl. No. 12/840,463.
USPTO NFOA dated Jun. 7, 2013; U.S. Appl. No. 13/141,606.
USPTO NFOA dated Jun. 8, 2012; U.S. Appl. No. 11/908,906.
USPTO NFOA dated Jun. 10, 2014; U.S. Appl. No. 13/167,492.
USPTO NFOA dated Jun. 14, 2016; U.S. Appl. No. 14/273,155.
USPTO NFOA dated Jun. 17, 2016; U.S. Appl. No. 14/357,040.
USPTO NFOA dated Jun. 18, 2015; U.S. Appl. No. 14/551,951.
USPTO NFOA dated Jul. 6, 2012; U.S. Appl. No. 12/692,061.
USPTO NFOA dated Jul. 2, 2012; U.S. Appl. No. 12/843,412.
USPTO NFOA dated Aug. 2, 2011; U.S. Appl. No. 12/435,291.
USPTO NFOA dated Aug. 4, 2010; U.S. Appl. No. 12/341,960.
USPTO NFOA dated Aug. 7, 2015; U.S. Appl. No. 14/128,756.
USPTO NFOA dated Aug. 22, 2014; U.S. Appl. No. 14/027,934.
USPTO NFOA dated Aug. 24, 2012; U.S. Appl. No. 12/563,930.
USPTO NFOA dated Aug. 26, 2014; U.S. Appl. No. 13/167,444.
USPTO NFOA dated Sep. 1, 2011; U.S. Appl. No. 12/706,868.
USPTO NFOA dated Sep. 19, 2014; U.S. Appl. No. 13/044,694.
USPTO NFOA dated Sep. 28, 2011; U.S. Appl. No. 12/437,103.
USPTO NFOA dated Sep. 29, 2014; U.S. Appl. No. 13/504,870.
USPTO NFOA dated Oct. 1, 2015; U.S. Appl. No. 14/141,228.
USPTO NFOA dated Oct. 3, 2014; U.S. Appl. No. 13/749,153.
USPTO NFOA dated Oct. 5, 2012; U.S. Appl. No. 12/996,954.
USPTO NFOA dated Oct. 5, 2015; U.S. Appl. No. 14/246,417.
USPTO NFOA dated Oct. 6, 2010; U.S. Appl. No. 12/484,512.
USPTO NFOA dated Oct. 14, 2014; U.S. Appl. No. 13/319,030.
USPTO NFOA dated Oct. 21, 2016; U.S. Appl. No. 14/567,472.
USPTO NFOA dated Nov. 14, 2011; U.S. Appl. No. 12/608,316.
USPTO NFOA dated Dec. 16, 2013; U.S. Appl. No. 13/666,262.
USPTO NFOA dated Dec. 18, 2013; U.S. Appl. No. 13/666,141.
USPTO NFOA dated Dec. 19, 2013; U.S. Appl. No. 14/027,934.
USPTO NFOA dated Dec. 29, 2011; U.S. Appl. No. 12/563,952.
USPTO NFOA dated Dec. 31, 2012; U.S. Appl. No. 13/044,694.
USPTO NOA dated Apr. 27, 2012; U.S. Appl. No. 12/341,960.
USPTO NOA dated May 6, 2016; U.S. Appl. No. 14/667,090.
USPTO NOA dated Sep. 16, 2016; U.S. Appl. No. 14/027,934.
USPTO mailed Jan. 3, 2017; U.S. Appl. No. 14/128,756.
USPTO NOA dated Jan. 7, 2014; U.S. Appl. No. 12/926,673.
USPTO NOA dated Jan. 22, 2015; U.S. Appl. No. 13/167,444.
USPTO NOA dated Jan. 29, 2016; U.S. Appl. No. 14/551,951.
USPTO NOA dated Feb. 2, 2015; U.S. Appl. No. 13/504,870.
USPTO NOA dated Feb. 19, 2014; U.S. Appl. No. 12/795,192.
USPTO mailed Mar. 1, 2017; U.S. Appl. No. 14/357,040.
USPTO NOA dated Mar. 23, 2011; U.S. Appl. No. 12/484,512.
USPTO NOA dated Mar. 25, 2015; U.S. Appl. No. 13/749,153.
USPTO NOA dated Apr. 3, 2013; U.S. Appl. No. 12/563,930.
USPTO NOA dated Apr. 12, 2016; U.S. Appl. No. 14/667,090.
USPTO NOA dated May 2, 2013; U.S. Appl. No. 12/843,412.
USPTO NOA dated May 22, 2013; U.S. Appl. No. 12/689,635.
USPTO NOA dated May 24, 2012; U.S. Appl. No. 12/563,952.
USPTO NOA dated Jun. 11, 2014; U.S. Appl. No. 12/689,693.
USPTO NOA dated Jun. 23, 2014; U.S. Appl. No. 12/548,991.
USPTO NOA dated Jun. 25, 2014; U.S. Appl. No. 13/666,262.
USPTO NOA dated Jun. 26, 2012; U.S. Appl. No. 12/608,316.
USPTO NOA dated Jul. 7, 2015; U.S. Appl. No. 12/996,954.
USPTO NOA dated Jul. 8, 2015; U.S. Appl. No. 13/707,013.
USPTO NOA dated Jul. 30, 2015; U.S. Appl. No. 13/319,007.
USPTO NOA dated Aug. 19, 2013; U.S. Appl. No. 11/908,906.
USPTO NOA dated Aug. 22, 2016; U.S. Appl. No. 14/084,426.
USPTO NOA dated Sep. 2, 2016; U.S. Appl. No. 14/027,934.
USPTO NOA dated Sep. 3, 2014; U.S. Appl. No. 12/689,693.
USPTO NOA dated Sep. 12, 2014; U.S. Appl. No. 11/950,930.
USPTO NOA dated Sep. 18, 2012; U.S. Appl. No. 12/706,868.
USPTO NOA dated Sep. 22, 2016; U.S. Appl. No. 13/740,582.
USPTO NOA dated Sep. 29, 2014; U.S. Appl. No. 13/141,606.
USPTO NOA dated Nov. 7, 2014; U.S. Appl. No. 13/167,492.
USPTO NOA dated Nov. 12, 2015; U.S. Appl. No. 13/319,007.
USPTO NOA dated Nov. 13, 2014; U.S. Appl. No. 12/795,026.
USPTO NOA dated Nov. 17, 2015; U.S. Appl. No. 14/486,226.
USPTO NOA dated Nov. 19, 2013; U.S. Appl. No. 12/795,192.
USPTO NOA dated Nov. 23, 2016; U.S. Appl. No. 14/141,228.
USPTO NOA dated Dec. 7, 2001; U.S. Appl. No. 12/435,291.
USPTO NOA dated Dec. 8, 2016; U.S. Appl. No. 14/246,417.
USPTO NOA dated Dec. 9, 2014; U.S. Appl. No. 13/167,476.
USPTO NOA dated Dec. 19, 2016; U.S. Appl. No. 14/242,151.
USPTO NOA dated Dec. 20, 2013; U.S. Appl. No. 12/437,103.
USPTO NOA dated Dec. 30, 2016; U.S. Appl. No. 13/319,030.
USPTO RR dated Jan. 6, 2012; U.S. Appl. No. 12/795,026.
USPTO RR dated Jan. 13, 2015; U.S. Appl. No. 13/707,013.
USPTO RR dated Jan. 23, 2012; U.S. Appl. No. 12/692,061.
USPTO RR dated Feb. 3, 2015; U.S. Appl. No. 14/084,426.
USPTO RR dated Feb. 4, 2013; U.S. Appl. No. 13/141,606.
USPTO RR dated Mar. 30, 2012; U.S. Appl. No. 12/785,717.
USPTO RR dated Apr. 1, 2011; U.S. Appl. No. 12/608,316.
USPTO RR dated Apr. 7, 2015; U.S. Appl. No. 13/319,007.
USPTO RR dated Apr. 19, 2010; U.S. Appl. No. 12/341,960.
USPTO RR dated May 1, 2012; U.S. Appl. No. 12/843,412.
USPTO RR dated May 5, 2011; U.S. Appl. No. 12/706,868.
USPTO RR dated May 19, 2011; U.S. Appl. No. 12/706,868.
USPTO RR dated May 28, 2015; U.S. Appl. No. 14/128,756.
USPTO RR dated Jun. 2, 2014; U.S. Appl. No. 13/319,030.
USPTO RR dated Jul. 5, 2012; U.S. Appl. No. 12/563,930.
USPTO RR dated Jul. 8, 2015; U.S. Appl. No. 14/141,228.
USPTO RR dated Jul. 12, 2011; U.S. Appl. No. 12/437,103.
USPTO RR dated Aug. 5, 2011; U.S. Appl. No. 11/908,906.
USPTO RR dated Aug. 12, 2012; U.S. Appl. No. 13/044,964.
USPTO RR dated Sep. 4, 2015; U.S. Appl. No. 14/589,100.
USPTO RR dated Sep. 14, 2012; U.S. Appl. No. 12/795,192.
USPTO RR dated Sep. 16, 2009; U.S. Appl. No. 11/950,930.
USPTO RR dated Sep. 17, 2012; U.S. Appl. No. 12/689,693.
USPTO RR dated Oct. 25, 2012; U.S. Appl. No. 13/167,444.
USPTO RR dated Oct. 27, 2011; U.S. Appl. No. 12/563,952.
USPTO RR dated Nov. 2, 2012; U.S. Appl. No. 13/167,492.
USPTO RR dated Nov. 14, 2011; U.S. Appl. No. 12/548,991.
USPTO RR dated Nov. 14, 2011; U.S. Appl. No. 12/689,635.
USPTO RR dated Nov. 19, 2012; U.S. Appl. No. 12/926,673.

(56) References Cited

OTHER PUBLICATIONS

USPTO Supplemental NOA dated Apr. 20, 2011; U.S. Appl. No. 12/484,512.
USPTO Supplemental NOA dated Nov. 18, 2016; U.S. Appl. No. 13/740,582.
USPTO Supplemental NOA dated Dec. 29, 2016; U.S. Appl. No. 14/246,417.

ACTIVELY-ENGAGEABLE MOVEMENT-RESTRICTION MECHANISM FOR USE WITH AN ANNULOPLASTY STRUCTURE

CROSS-REFERENCES TO RELATED APPLICATIONS

The present application is a continuation application of U.S. Ser. No. 13/740,582 to Miller et al., entitled, "Actively-engageable movement-restriction mechanism for use with an annuloplasty structure," filed on Jan. 14, 2013, which issued as U.S Pat. No. 9,561,104, and which is a divisional application of U.S. Ser. No. 12/706,868 to Miller entitled, "Actively-engageable movement-restriction mechanism for use with an annuloplasty structure," filed on Feb. 17, 2010, which issued as U.S. Pat. No. 8,353,956 and which claims the priority from US Provisional Patent Application 61/207,908 to Miller et al., entitled, "Actively-engageable movement-restriction mechanism for use with an annuloplasty structure," filed on Feb. 17, 2009.

These applications and patents are assigned to the assignee of the present application and incorporated herein by reference.

FILED OF THE INVENTION

Some applications of the present invention relate in general to valve repair. More specifically, some applications of the present invention relate to repair of a mitral valve of a patient.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

US Patent Application Publications 2004/0260393 to Randert et al. and 2004/0127982 to Machold et al. describe techniques using an implant that is sized and configured to attach in, on, or near the annulus of a dysfunctional heart valve. In use, the implant extends either across the minor axis of the annulus, or across the major axis of the annulus, or both. The implant is described as restoring to the heart valve annulus and leaflets a more functional anatomic shape and tension. The more functional anatomic shape and tension are conducive to coaptation of the leaflets, which, in turn, reduces retrograde flow or regurgitation. In some embodiments, the implant is configured to rest at or near a heart valve annulus and apply a direct mechanical force along the minor axis of the annulus to inwardly displace tissue toward the center of the annulus. For some applications, the implant is configured to extend significantly above the plane of the valve, while for other applications, the implant is configured to extend a short distance above the plane of the valve.

U.S. Pat. No. 7,500,989 to Solem et al. describes devices and methods for treating mitral regurgitation by reshaping the mitral annulus in a heart. One device for reshaping the mitral annulus is provided as an elongate body having dimensions as to be insertable into a coronary sinus. The elongate body includes a proximal frame having a proximal anchor and a distal frame having a distal anchor. A ratcheting strip is attached to the distal frame and an accepting member is attached to the proximal frame, wherein the accepting member is adapted for engagement with the ratcheting strip. An actuating member is provided for pulling the ratcheting strip relative to the proximal anchor after deployment in the coronary sinus. In one embodiment, the ratcheting strip is pulled through the proximal anchor for pulling the proximal and distal anchors together, thereby reshaping the mitral annulus.

The following patents and patent applications may be of interest:

EP Patent EP 06/14342 to Pavcnik et al.
EP Patent EP 10/06905 to Organ
PCT Publication WO 00/22981 to Cookston et al.
PCT Publication WO 01/26586 to Seguin
PCT Publication WO 01/56457 to Pruitt
PCT Publication WO 05/046488 to Douk et al.
PCT Publication WO 06/012013 to Rhee et al.
PCT Publication WO 06/086434 to Powell et al.
PCT Publication WO 06/097931 to Gross et al.
PCT Publication WO 06/105084 to Cartledge et al.
PCT Publication WO 96/39963 to Abela et al.
PCT Publication WO 96/40344 to Stevens-Wright et al.
PCT Publication WO 97/01369 to Taylor et al.
PCT Publication WO 98/46149 to Organ
U.S. Pat. No. 3,656,185 to Carpentier
U.S. Pat. No. 4,961,738 to Mackin
U.S. Pat. No. 5,325,845 to Adair
U.S. Pat. No. 5,593,424 to Northrup III
U.S. Pat. No. 5,716,370 to Williamson, IV et al.
U.S. Pat. No. 5,855,614 to Stevens et al.
U.S. Pat. No. 6,074,401 to Gardiner et al.
U.S. Pat. No. 6,102,945 to Campbell
U.S. Pat. No. 6,619,291 to Hlavka et al.
U.S. Pat. No. 6,918,917 to Nguyen et al.
U.S. Pat. No. 6,926,730 to Nguyen et al.
U.S. Pat. No. 7,150,737 to Purdy et al.
U.S. Pat. No. 7,172,625 to Shu et al.
U.S. Pat. No. 7,175,660 to Cartledge et al.
U.S. Pat. No. 7,226,467 to Lucatero et al.
US Patent Application Publication 2003/0078465 to Pai et al.
US Patent Application Publication 2003/0199974 to Lee et al.
US Patent Application Publication 2004/0127983 to Mortier et al.
US Patent Application Publication 2004/0148021 to Cartledge et al.
US Patent Application Publication 2004/0260394 to Douk et al.
US Patent Application Publication 2005/0055038 to Kelleher et al.
US Patent Application Publication 2005/0096740 to Langberg et al.
US Patent Application Publication 2006/0095009 to Lampropoulos et al.
US Patent Application Publication 2006/0195134 to Crittenden
US Patent Application Publication 2006/0282161 to Huynh et al.

US Patent Application Publication 2006/0247763 to Slater

US Patent Application Publication 2008/0027483 to Cartledge et al.

US Patent Application Publications 2004/0148019 and 2004/0148020 to Vidlund et al.

The following articles, which are incorporated herein by reference, may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

SUMMARY OF THE INVENTION

In some embodiments of the present invention, systems and methods are provided for contracting an annuloplasty structure in order to repair a dilated mitral valve of a patient. The annuloplasty structure comprises an annuloplasty ring. The annuloplasty structure is compressible at least in part and has a lumen therethrough. A movement-restriction mechanism is disposed within the lumen of the annuloplasty structure and is selectively and actively engageable. The movement-restriction mechanism comprises a strip of flexible metal having first and second ends. The first end of the strip is moveable with respect to the second end of the strip, which is typically fixed to a housing coupled to the annuloplasty structure. At least a portion of the strip, e.g., the portion which is disposed adjacently to the first end, is shaped to provide a plurality of recesses that are engageable by a recess-engaging portion that is coupled to the housing.

Typically, the recess-engaging portion is coupled to a lever arm and the recess-engaging potion and/or the lever arm is reversibly coupled to a mechanical support which maintains a position of the recess-engaging potion with respect to the strip in which the recess-engaging portion does not engage any of the recesses of the strip. When none of the recesses are engaged by the recess-engaging portion, the first end slides freely in either direction with respect to the second end of the strip. Once the mechanical support is actively released from the recess-engaging potion and/or from the lever arm, the recess-engaging portion is positioned within one of the recesses of the strip, thereby locking in place the strip and restricting motion in either direction of the first end of the strip with respect to the second end of the strip.

The annuloplasty structure is shaped to provide a primary, outer body portion having at least a first portion comprising a material, e.g., a coil, that is longitudinally-compressible. The annuloplasty structure comprises a secondary body portion comprising a compressible element, e.g., a tubular coil, that is disposed within a lumen provided by the primary body portion. Portions of the secondary body portion are coupled to a surface of a portion of the strip of the movement-restriction mechanism. Typically, the system comprises a flexible member, e.g., a wire, that functions to compress and contract the annuloplasty structure. The flexible member is typically disposed within a lumen provided by the secondary compressible element. When the annuloplasty structure comprises an annuloplasty ring, the secondary compressible element is coupled to an outer surface of the ring-shaped strip. The secondary compressible element ensures that the flexible member is maintained at an outer perimeter of the ring-shaped strip.

The first end of the strip passively slides in a first direction with respect to the second end of the strip, in response to active pulling on first and second ends of the flexible member. That is, the first end of the strip is not pulled by the flexible member, but rather is passively pushed in response to the contracting of the flexible member. As the first end of the strip slides in the first direction with respect to the second end, and the strip contracts to assume a smaller perimeter than in its resting state, the compressible element of the primary body portion of the annuloplasty structure contracts to assume a smaller perimeter, in turn. When the flexible member is released and is allowed to relax, the first end slides in a second direction with respect to the second end, and in turn, the perimeter of the strip is enlarged and the compressible element of the body portion expands.

Thus, the selectively-engageable movement-restriction mechanism facilitates unobstructed contraction and expansion of the annuloplasty structure, and thereby unobstructed adjustment of a perimeter thereof. When a desired perimeter of the annuloplasty structure is achieved, the mechanical structure is actively released which releases recess-engaging portion such that it engages a recess of the strip, thereby locking in place the strip and restricting further contraction and expansion of the annuloplasty structure.

There is therefore provided, in accordance with some applications of the present invention, apparatus, including:
a locking mechanism;
an implant shaped so as to define a lumen therethrough; and
a flexible strip disposed at least in part within the lumen, the strip shaped so as to define:
a first end,
a second end, and
a plurality of recesses,
the first and second ends coupled to the locking mechanism such that the strip defines a closed loop and a perimeter thereof which (a) shortens when the first end is advanced through the locking mechanism in a first direction thereof and (b) expands when the first end is advanced in a second direction opposite the first direction,
and the locking mechanism includes:
a moveable recess-engaging portion;
a mechanical support, removably coupled to the recess-engaging portion; and
a force applicator which maintains the recess-engaging portion in a position in which the recess-engaging portion is not disposed in any of the recesses and which, upon decoupling of the mechanical support from the recess-engaging portion, restricts motion of the plurality of recesses of the strip with respect to the second end of the strip, by facilitating positioning of the recess-engaging portion in one of the plurality of recesses.

In some applications, the force applicator includes a spring.

In some applications, for each one of the recesses, the strip is shaped to provide first and second opposing walls which define the recess, the first wall having a dimension that is substantially the same as a dimension of the second wall.

In some applications, the implant includes expanded polytetrafluoroethylene (ePTFE).

In some applications, the implant is coated with polytetrafluoroethylene.

In some applications, the apparatus is configured to be implanted along an annulus of a mitral valve of a patient, and the apparatus is configured to be transcatheterally advanced toward the annulus.

In some applications the apparatus includes a flexible member disposed within the lumen of the implant and alongside the strip, the flexible member being configured push against the strip to contract the strip and facilitate passive advancement of the first end of the strip through the locking mechanism.

In some applications:
the implant is configured to be implanted along an annulus of a mitral valve of a patient,
the flexible member is configured to contract the implant when the flexible member is pulled, and
the implant is configured to contract the annulus in response to the contraction thereof.

In some applications:
the implant includes an outer body portion shaped to define the lumen,
when formed into the closed loop, the flexible strip is shaped to provide an inner surface and an outer surface, and
the apparatus further includes an inner body portion coupled at least a portion thereof to the outer surface of the strip, the inner body portion being shaped so as to define an inner body lumen therethrough.

In some applications the apparatus includes a flexible member configured for slidable advancement through the inner body lumen, the flexible member being configured to push against the strip to contract the strip and to facilitate passive advancement of the first end of the strip with respect to the second end of the strip.

In some applications, the inner body portion is compressible.

In some applications, the inner body portion includes expanded polytetrafluoroethylene (ePTFE).

In some applications:
the apparatus is configured to be implanted along an annulus of a mitral valve of a heart of a patient,
a first section of the implant is flexible and longitudinally-compressible, and
a second section in series with the first section of the implant, the second section being flexible and less longitudinally-compressible than the first section.

In some applications, the second section is not longitudinally-compressible.

In some applications, a radius of curvature at a center of the first section is smaller than a radius of curvature at a center of the second section, when no external force is applied to the implant.

In some applications, the second section of the implant has first and second ends thereof and a body portion disposed between the first and second ends, the second section of the implant being configured to be disposed along a portion of the annulus in a manner in which:
the first end of the second section is configured to be coupled to the annulus in a vicinity of a left trigone of the heart that is adjacent to the mitral valve of the patient,
the second end of the second section is configured to be coupled to the annulus in a vicinity of a right trigone of the heart that is adjacent to the mitral valve, and
the body portion is configured to be disposed along the annulus in a vicinity of the annulus that is between the left and right trigones.

In some applications, the body portion disposed between the first and second ends of the second section of the implant has a length of 10-50 mm.

There is further provided, in accordance with some applications of the present invention, a method, including:
providing an implant shaped so as to define a lumen therethrough and a flexible strip disposed at least in part within the lumen of the implant, the strip having:
a first end,
a second end, and
a plurality of recesses, and
a locking mechanism to which the first and second ends of the strip are coupled such that the strip defines a closed loop and a perimeter thereof which (a) shortens when the first end is advanced through the locking mechanism in a first direction thereof and (b) expands when the first end is advanced in a second direction opposite the first direction;
advancing the first end of the strip in first and second opposing directions with respect to the second end of the strip;
maintaining a recess-engaging portion in a position in which the recess-engaging portion is not disposed in any of the plurality of recesses during the advancing; and
restricting the advancing by facilitating active positioning of the recess-engaging portion in one of the plurality of recesses.

In some applications the method includes, coupling the implant along an annulus of a mitral valve of a patient.

In some applications the method includes, advancing the implant transcatheterally toward an annulus of a patient.

In some applications, advancing the portion of the strip in first and second opposing directions with respect to the second end of the strip includes contacting and expanding the implant, respectively.

In some applications the method includes, coupling the implant along an annulus of a mitral valve of a patient, and contacting and expanding the implant includes contacting and expanding the annulus, respectively.

There is also provided, in accordance with some applications of the present invention, apparatus, including:
an implant including a flexible longitudinal member having first and second ends that are opposable to form the longitudinal member into a closed loop having a perimeter thereof which (a) shortens when the first end is advanced in a first direction with respect to the second end in a first direction thereof and (b) expands when the first end is advanced with respect to the second end in a second direction opposite to the first direction, and
when formed into the closed loop, the longitudinal member is shaped to provide an inner surface and an outer surface with respect to a center of the closed loop;
a body portion coupled at least a portion thereof to the outer surface of the longitudinal member, body portion being shaped so as to define a lumen therethrough; and
a flexible contracting member being disposed within and slidably advanceable through the lumen to facilitate a modulation of a perimeter of the body portion, which, in turn facilitates a modulation of a perimeter of the longitudinal member.

In some applications the apparatus includes, a tubular structure shaped so as to define a tubular structure lumen therethrough, and:

the flexible longitudinal member is disposed at least in part within the tubular structure lumen, and the longitudinal member is configured to facilitate a modulation of a perimeter of the tubular structure in response to the modulation of the perimeter of the longitudinal member.

In some applications, the implant includes an annuloplasty ring.

The present invention will be more fully understood from the following detailed description of embodiments thereof, taken together with the drawings, in which:

DETAILED DESCRIPTION OF THE EMBODIMENTS

Figure 1:
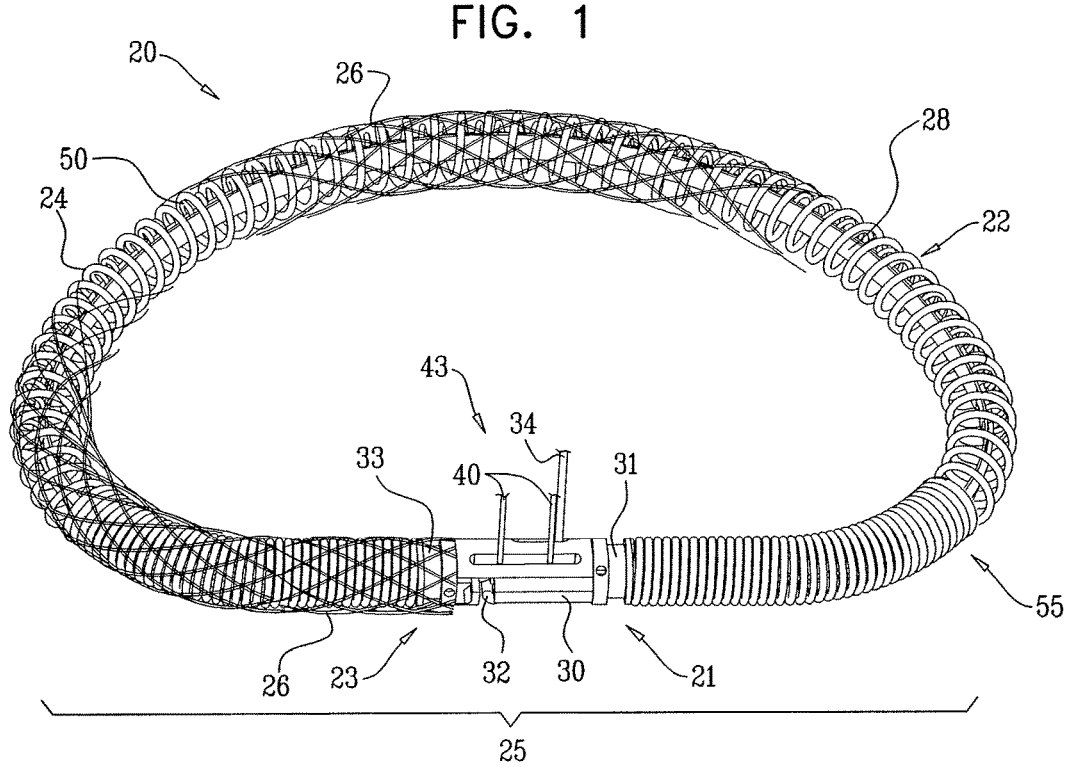
FIG. 1 is a schematic illustration of an annuloplasty ring structure, in accordance with some embodiments of the present invention.
Figure 2A:
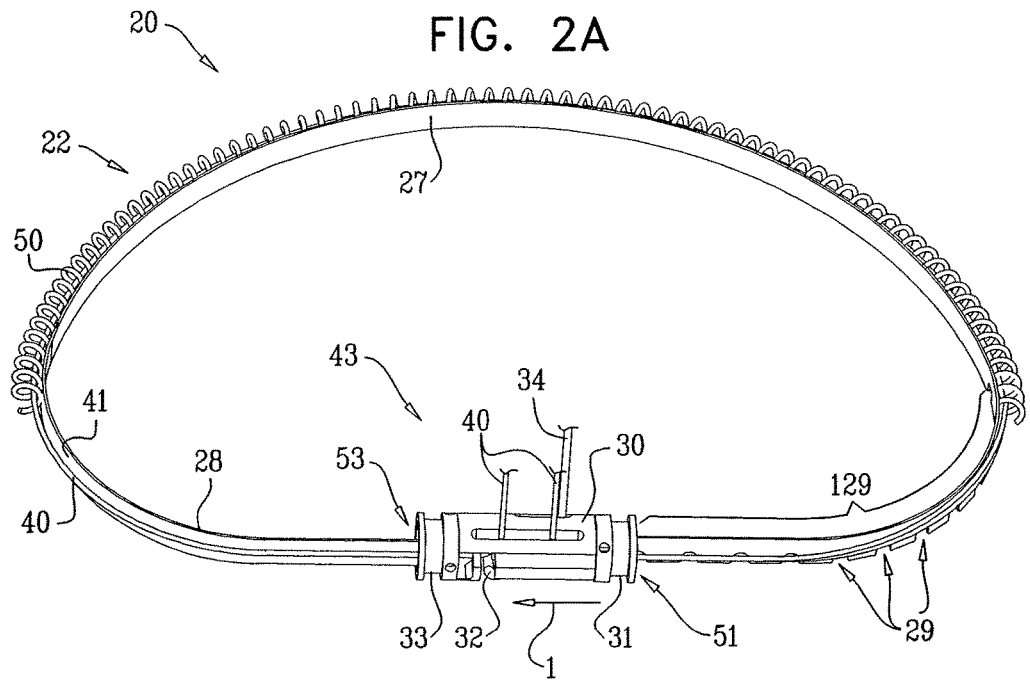
FIGS. 2A-C are schematic illustrations of an inner compressible element disposed within a lumen of the ring structure of FIG. 1, in accordance with some embodiments of the present invention.
Figure 2B:
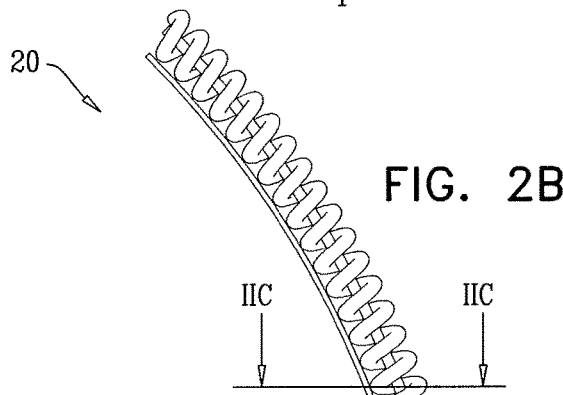
Figure 2C:
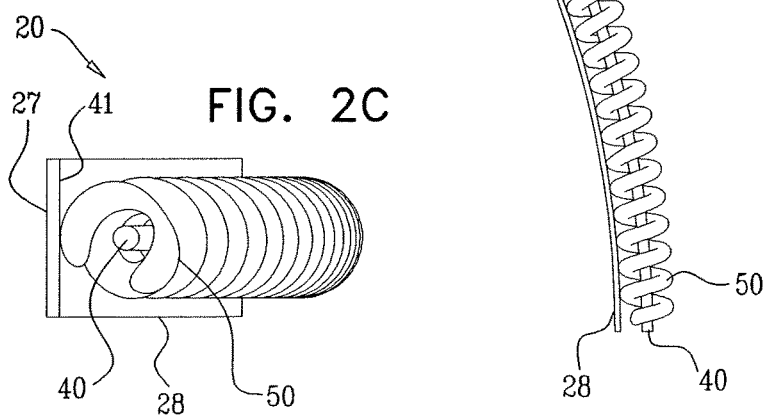
Figure 3:
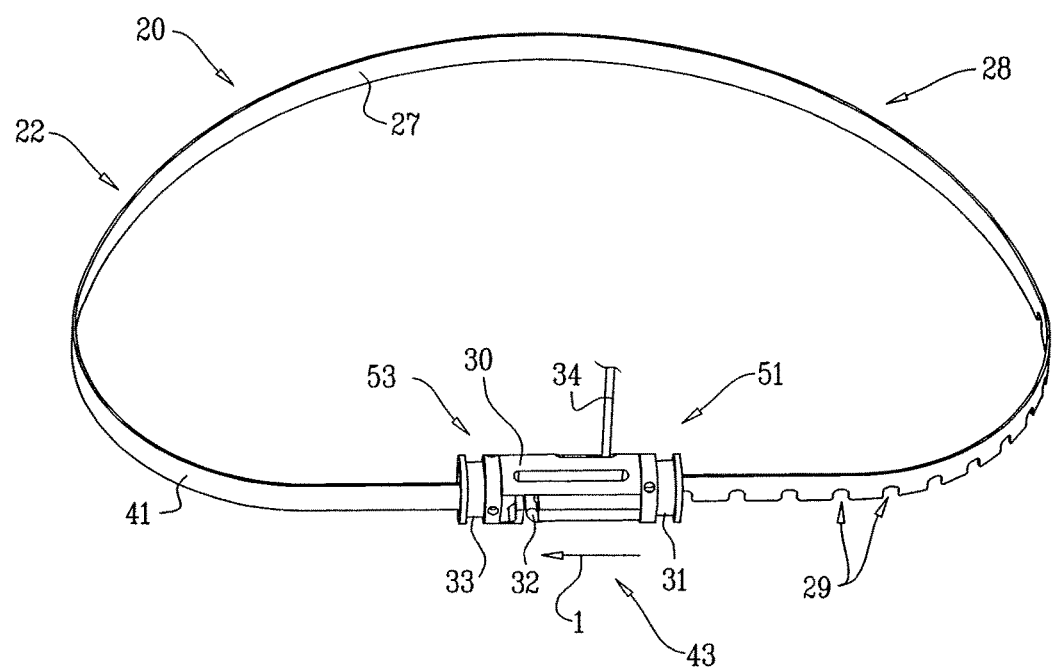
FIG. 3 is a schematic illustration of a movement-restriction mechanism comprising a strip coupled to the compressible element of FIGS. 2A-C, in accordance with some embodiments of the present invention.

Reference is now made to FIGS. 1-3, which are schematic illustrations of an annuloplasty structure 20 comprising an annuloplasty ring 22 having a tubular outer body portion 55 and a tubular inner body portion 50, and a movement-restriction mechanism comprising a flexible strip 28, in accordance with some embodiments of the present invention. Typically, strip 28 comprises a flexible longitudinal member comprising a flat band or ribbon. Outer body portion 55 comprises a compressible portion 24 and one or more less-compressible portions 25. For example, compressible portion may comprise a coiled element, as shown by way of illustration and not limitation. For some applications, compressible portion 24 may comprise stent-like struts, or a braided mesh. Typically, structure 20 comprises a tubular structure defining a substantially longitudinal lumen which houses a flexible contracting member 40 and strip 28 of the movement-restriction mechanism. Typically, body portion 55 is surrounded by a braided mesh. Compressible portion 24 and the braided mesh surrounding body portion 55 are configured for the advancement therethrough of tissue anchors and/or sutures which anchor, suture, or otherwise couple structure 20 to the native annulus of the heart valve.

At least a portion of strip 28 is configured for slidable advancement within the lumen of structure 20 in response to the pulling or pushing of flexible member 40. When flexible member 40 is tightened, or pulled, the portion of strip 28 is made to slide in a first direction, and, consequently, a perimeter of strip 28 is reduced, or shortened, thereby compressing and contracting structure 20 such that a perimeter thereof is, in turn, reduced. When flexible member 40 is loosened, the portion of strip 28 is made to slide in a second direction opposite the first, and, consequently, a perimeter of strip 28 is enlarged thereby expanding structure 20 such that a perimeter thereof is, in turn, enlarged.

In addition to facilitating a modulation of the perimeter of structure 20, strip 28 functions to (a) provide a scaffold for stabilizing and maintaining the spatial configuration of structure 20 and for supporting the lumen provided by outer body portion 55, and (b) prevent crushing or collapsing of ring 22. Additionally, since strip 28 comprises nitinol (by way of illustration and not limitation), strip 28 is flexible and has elastic shape-memory to form structure 20 into a D-shaped closed configuration. It is to be noted that ring 22 may be shaped to define any suitable configuration, e.g., a saddle shape, an oval shape, an elliptical shape, etc.

Typically, a filler material (e.g., polyester, polytetrafluoroethylene (PTFE), polyethylene terephthalate (PET), or expanded polytetrafluoroethylene (ePTFE)) is packed within at least a portion, e.g., 50%, 75%, or 100%, of the lumen of outer body portion 55. The filler material functions to prevent (1) formation within the lumen provided by outer body portion 55 of clots or (2) introduction of foreign material into the lumen which could obstruct the sliding movement of strip 28 and flexible member 40.

Compressible portion 24 is compressible along a longitudinal axis of the lumen defined by structure 20. Structure 20 has first and second ends 21 and 23 which are coupled to a locking mechanism 43. Locking mechanism 43 comprises a housing 30 having first and second coupling members 31 and 33 to which are coupled, e.g., welded or otherwise fastened, to first and second ends 21 and 23, respectively, of structure 20. Housing 30 facilitates (a) the advancement, in either direction, of a first end of strip 28 with respect to a second end of strip 28, and (b) selective, active locking of strip 28 with respect to housing 30.

Flexible member 40 comprises a flexible and/or superelastic material, e.g., nitinol, polyester, stainless steel, or cobalt chrome, and is configured to reside permanently within structure 20. In some embodiments, flexible member 40 comprises a braided polyester suture (e.g., Ticron). In some embodiments, flexible member 40 is coated with polytetrafluoroethylene (PTFE). In some embodiments, flexible member 40 comprises a plurality of wires that are intertwined to form a rope structure.

FIG. 1 shows an assembly of components shown in FIGS. 2A-C and 3. As shown in FIG. 1, structure 20 comprises compressible portion 24 and less-compressible portion 25, which is less longitudinally-compressible than portion 24, e.g., not longitudinally-compressible. Typically, compressible portion 24 and less-compressible portion 25 are surrounded by a braided mesh 26 (for clarity of illustration, portions of ring 22 are shown as not being surrounded by mesh 26). Typically, braided mesh 26 comprises a flexible material, e.g., metal or fabric such as polyester, and is longitudinally-compressible.

Typically, compressible portion 24 and less-compressible portion 25 comprise a flexible, biocompatible material, e.g., nitinol, stainless steel, platinum iridium, titanium, expanded polytetrafluoroethylene (ePTFE), or cobalt chrome. For some applications, portions 24 and 25 are coated with PTFE (Polytetrafluoroethylene). In some embodiments, compressible portion 24 comprises accordion-like compressible structures (configuration not shown) which facilitate proper cinching of the annulus when structure 20 is contracted.

Longitudinal compression of compressible portion 24 enables portions of annuloplasty ring 22 to contract and independently conform to the configuration of the annulus of the mitral valve of a given patient. Thus, since structure 20 is sutured or otherwise anchored to the annulus, the compression of compressible portion 24 facilitates the contraction of structure 20, and responsively thereto, the contraction of the annulus.

Structure 20 defines a substantially ring-shaped configuration, e.g., a "D"-shaped configuration, as shown, which conforms to the shape of the annulus of a mitral valve of the patient. Prior to the contracting of structure 20, compressible portion 24 is relaxed and structure 20 defines a first perimeter thereof. Portion 25 is configured to be disposed along the fibrous portion of the annulus that is between the trigones of the mitral valve of the heart when structure 20 is anchored, sutured, fastened or otherwise coupled to the annulus of the mitral valve. Less-compressible portion 25 imparts rigidity to structure 20 in the portion thereof that is disposed between the fibrous trigones such that structure 20 mimics the conformation and functionality of the mitral valve. Typically, portion 25 has a length of 10-50 mm. Additionally, during contraction of structure 20 responsively to the pulling of flexible member 40, less-compressible portion 25 minimizes the need for additional compression forces on the portions of structure 20 which lie adjacently to portions of the native annulus which do not need to be and/or cannot be contracted.

Thus, structure 20 defines a compressible portion and a less-compressible portion. Typically, a radius of curvature at a center of compressible portion 24 is less than a radius of curvature at a center of less-compressible portion 25, when no external force is applied to annuloplasty structure 20.

It is to be noted that compressible portion 24 and less-compressible portion 25 comprise coiled elements by way of illustration and not limitation. For example, compressible portion 24 and less-compressible portion 25 may comprise stent-like struts, or a braided mesh. In either configuration, portion 25 is permanently longitudinally compressed when ring 22 is in a resting state.

Reference is now made to FIGS. 2A and 3. FIG. 2A shows inner body portion 50 and strip 28 of structure 20, in accordance with some embodiments of the present invention. For clarity of illustration, structure 20 is shown without surrounding outer body portion 55 (as illustrated hereinabove with reference to FIG. 1). Typically, inner body portion 50 and strip 28 are disposed within the lumen provided by outer body portion 55. Strip 28 comprises a flexible material, e.g. nitinol, and has first and second ends 51 and 53 which are opposable to form strip 28 into a substantially closed loop, ring-shaped configuration. Typically, second end 53 of strip 28 is coupled to locking mechanism 43 by being fixed to housing 30, while first end 51 of strip 28 is dynamic and is advanceable in either direction with respect to second end 53. That is, first end 51 is reversibly coupled to locking mechanism 43. When both first and second ends 51 and 53 are coupled to locking mechanism 43, strip 28 is formed into a closed loop. Strip 28 is shaped to provide a recesses portion 129 which is shaped to define a plurality of recesses 29. Typically, recesses portion 129 is provided adjacent to first end 51 of strip 28, as shown by way of illustration and not limitation. It is to be noted that recesses portion 129 may be provided at any suitable location along strip 28. As shown in FIG. 3, the opposing walls on either side of each recess 29 (i.e., the walls that define recess 29) have substantially the same height and angle, i.e., 90 degrees with respect to the longitudinal axis of structure 20, as shown.

Reference is again made to FIG. 2A. A portion of flexible member 40 surrounds strip 28 along an outer perimeter of the strip. Housing 30 of locking mechanism 43 is shaped to define at least one opening through which first and second portions of flexible member 40 emerge from structure 20. Typically, the first and second portions of flexible member 40 extend to a site outside the body of the patient. In response to a pulling force applied to one or both of first and second portions of flexible member 40, the portion of flexible member 40 that surrounds strip 28 contracts. In response to the contraction, flexible member 40 applies a force to and pushes against strip 28, thereby contracting strip 28. As the force is applied to strip 28 by flexible member 40, first end 51 of strip 28 slides with respect to second end 53 of strip 28, as indicated by an arrow 1, thereby reducing a perimeter of strip 28 and ring 22. As the perimeter of ring 22 is reduced, compressible portion 24 contracts longitudinally and facilitates radial contraction of ring 22.

Strip 28, when formed into a substantially ring-shaped configuration, provides an inner surface 27 and an outer surface 41 with respect to a center of the ring-shaped, closed-loop configuration of strip 28 and ring 22. Inner body portion 50 is typically welded, or otherwise coupled, at respective locations to outer surface 41 of strip 28 (as shown in FIGS. 2A-C). Inner body portion 50 comprises a compressible material, e.g., nitinol, stainless steel, platinum iridium, titanium, expanded polytetrafluoroethylene (ePTFE), or cobalt chrome. In some embodiments, inner body portion 50 is coated with PTFE (polytetrafluoroethylene). Inner body portion 50 is shaped to define a plurality of coils, by way of illustration and not limitation. For some applications, inner body portion 50 may comprise accordion-like compressible structures (configuration not shown). In some embodiments, outer and inner body portions 55 and 50 are shaped to define a tubular structure comprising a compressible material, e.g., ePTFE. In response to the contracting of outer body portion 55 of structure 20: (1) the perimeter of outer body portion 55 is reduced such that outer body portion 55 pushes against strip 28, (2) in response to the pushing of strip 28, the first end of the strip slides in with respect to the second end of the strip such that the perimeter of strip is reduced, and (3) in response to the contracting of the strip, the inner body portion 50 contracts.

FIG. 2C shows a portion of strip 28, inner body portion 50, and flexible member 40 at a cross-section of strip 28, inner body portion 50, and flexible member 40, as shown in FIG. 2B. As shown in FIG. 2C, inner body portion 50 is shaped to provide a lumen for slidable advancement therethrough of a portion of flexible member 40. Because flexible member 40 is housed in the lumen of inner body portion 50, the flexible member remains disposed along outer surface 41, i.e., at an outer perimeter of strip 28, and is restricted from sliding above or below strip 28 and toward inner surface 27, i.e., an inner perimeter of strip 28. Such a configuration ensures that flexible member 40 remains disposed along outer surface 41 of strip 28 such that flexible member 40, in response to a pulling force applied thereto, appropriately applies a contraction force to strip 28.

Flexible member 40, by being disposed within and slidably advanceable through the lumen of inner body portion 50, facilitates a modulation of a perimeter of inner body portion 50, which, in turn facilitates a modulation of a perimeter of strip 28, and ultimately, outer body portion 55.

Figure 4:
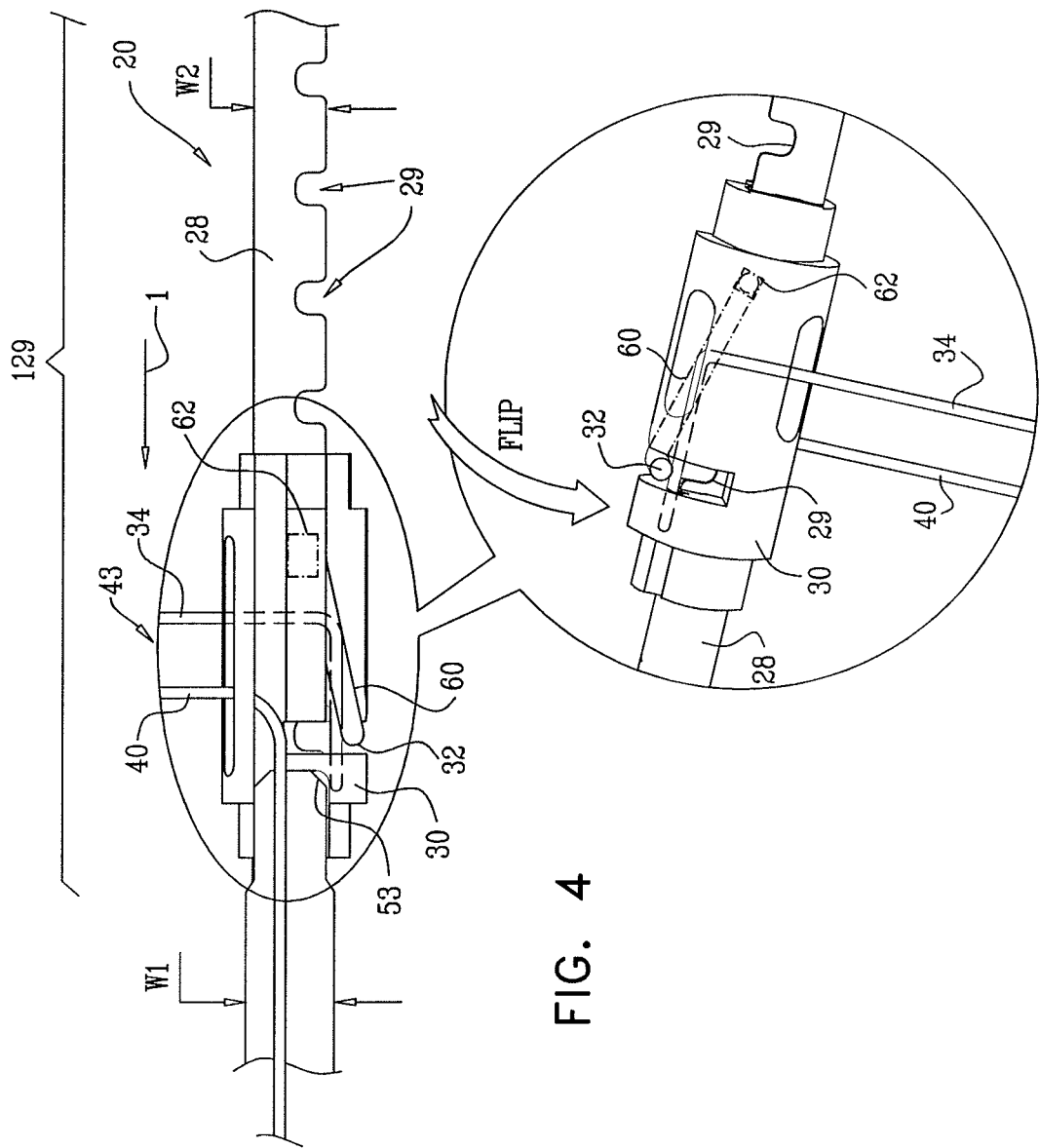
FIG. 4 is a schematic illustration of a locking mechanism to lock a configuration of the strip of FIG. 3, in accordance with some embodiments of the present invention.

Reference is now made to FIG. 4, which shows locking mechanism 43 of structure 20 comprising housing 30 and a motion restrictor 60 which is actively engageable by a mechanical support 34, in accordance with some embodiments of the present invention. Motion restrictor 60 comprises a recess-engaging portion 32 that is coupled to a lever arm, which, in turn, is coupled to housing 30 by a force applicator 62. Typically, force applicator 62 comprises a mechanical spring, by way of illustration and not limitation, which causes motion of recess-engaging portion 32 with respect to housing 30. Force applicator 62 creates a tendency for the lever arm and recess-engaging portion 32 to assume a position in which recess-engaging portion 32 engages one of recesses 29 of strip 28. In order to restrict such a tendency, locking mechanism 43 comprises a mechanical support 34 which maintains recess-engaging portion 32 in a position in which recess-engaging portion 32 does not engage any of recesses 29. Mechanical support 34 comprises a flexible rod or string which is (a) removably coupled at a first end thereof to housing 30, and (b) accessible by an operating physician at a second end thereof. Support 34 comprises a portion adjacent to the first end of the support which functions to block recess-engaging portion 32 from engaging any of recesses 29. That is, recess-engaging portion 32 rests against the portion of support 34.

Typically, recesses portion 129 of strip 28 is narrower than the rest of the portions of strip 28. That is, strip 28 has a width W1 of 1.6-1.9 mm, e.g., 1.6 mm while recesses portion 129 has a width W2 of within the lumen provided by primary body portion 55 1.2-1.5 mm, e.g., 1.3 mm. Width W2 of recesses portion 129 allows recesses portion 129 to slide along inner surface 27 of a portion of strip 28 adjacent to second end 53, while not being obstructed by the inner wall of outer body portion 55 which surrounds the lumen of outer body portion 55.

Figure 5:
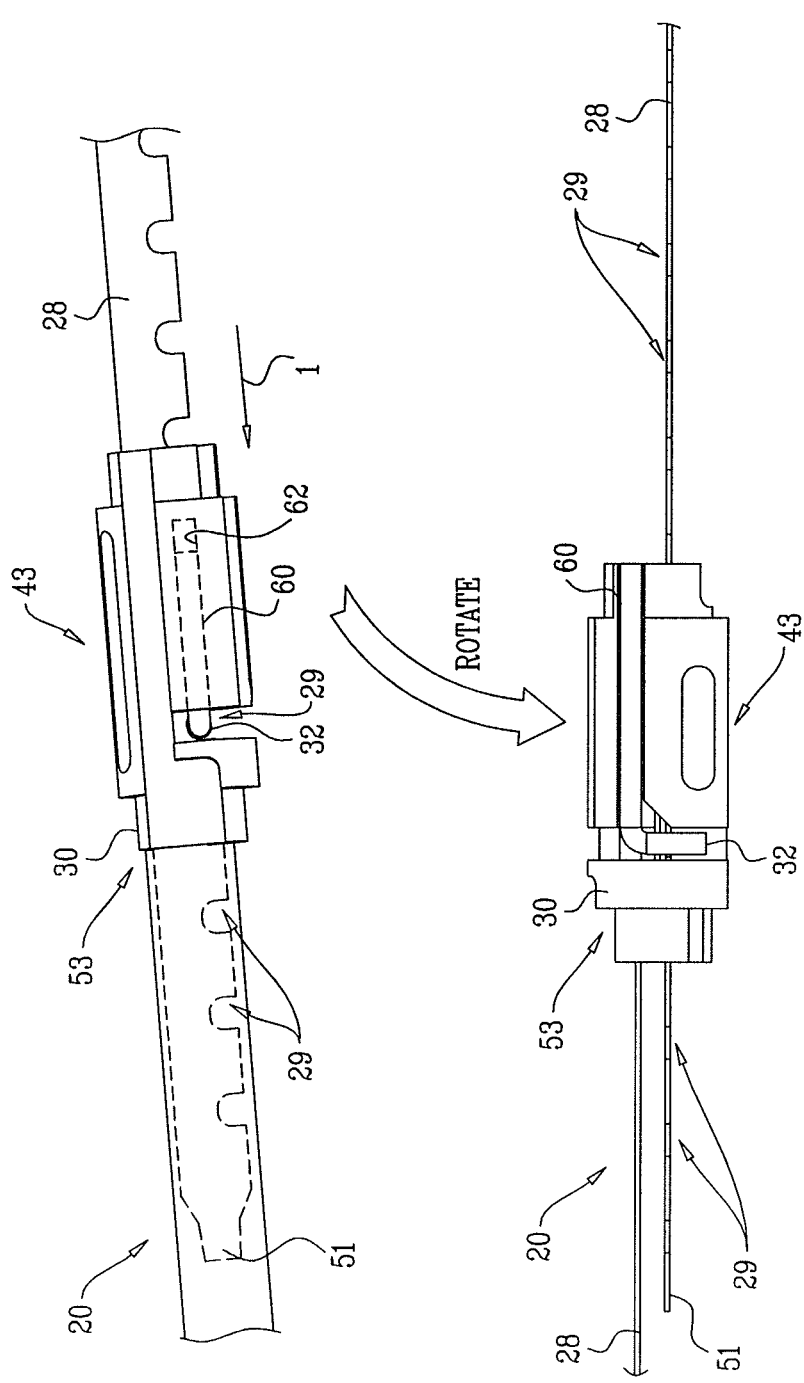
FIG. 5 is a schematic illustration of the locking mechanism in a locked state, in accordance with some embodiments of the present invention.

In such a configuration, first end 51 of strip 28 may be advanced bidirectionally with respect to second end 53 of strip 28 and housing 30, and thereby facilitates contraction and expansion of structure 20 in order to control the perimeter of structure 20. Once the physician achieves a desired perimeter length of structure 20, the physician actively and selectively engages locking mechanism 43. By pulling on mechanical support 34 from a site outside the body of the patient, the first end of support 34 is disengaged and removed from housing 30, thereby allowing recess-engaging portion 32 to engage one of recesses 29, as shown in FIG. 5.

As shown in FIGS. 2A, 3, 4, and 5, second end 53 of strip 28 is fixed to housing 30 in a vicinity of recess-engaging portion 32. In some embodiments, a flexible, curved secondary scaffold portion (not shown) is coupled to housing 30 in a vicinity of housing 30 that is opposite to second end 53 of strip 28 (i.e., the side of housing 30 through which first end 51 of strip 28 is introduced within housing 30 and slides therethrough) and extends away from housing 30. The secondary scaffold portion is disposed within outer body portion 55 and has a dimension of between 50 and 120 degrees of structure 20 in its closed loop configuration. In some embodiments, the secondary scaffold portion has a dimension that is substantially equal to or less than the dimension of recesses portion 129. The secondary scaffold portion may be shaped to define a strip, a tube, or a rod, and comprises a flexible material, e.g., nitinol, which provides a balancing force to structure 20 as first end 51 of strip 28 is advanced beyond housing 30 and away from the secondary scaffold portion.

In some embodiments of the present invention, the contraction of strip 28 and thereby structure 20 is reversible. In other words, releasing flexible member 40 following its tightening, slackens the portion of flexible member 40 surrounding strip 28. Responsively, annuloplasty structure 20 gradually relaxes (i.e., with respect to its contracted state) as the compressible portions of outer body portion 55 and inner body portion 50 gradually expand. As the compressible portions expand, first end 51 of strip 28 slides with respect to second end 53 in the direction opposite that in which it is slid during contraction of structure 20.

It is to be noted that for some embodiments, second end 53 of strip 28 is not fixed to ring 22. For example, both first and second ends 51 and 53 of strip 28 may be configured for slidable advancement through the lumen of structure 20. That is, first and second ends 51 and 53 of strip 28 may be advanceable with respect to each other in opposite directions.

FIG. 5 shows locking mechanism 43 locking strip 28 in place, in accordance with some embodiments of the present invention. The lower illustration of FIG. 5 shows a 90 degree flip along a y-axis of the upper image of FIG. 5. Once the physician determines that the annuloplasty ring structure has assumed a desired perimeter, the physician pulls on mechanical support 34, as described hereinabove with reference to FIG. 4. Mechanical support 34 is pulled away from housing 30 of locking mechanism 43 which allows for the lever arm of motion restrictor 60 to pivot along force applicator 62 such that motion restrictor 60 assumes a configuration in which (1) the lever arm of motion restrictor 60 lies in parallel with a longitudinal axis of housing 30, and (2) recess-engaging portion 32 is disposed within one of recesses 29 of strip 28, as shown in FIG. 5.

Once recess-engaging portion 32 is disposed within recess 29, motion of the first end 51 of strip 28 with respect to the second end 53 of strip 28 is restricted and a perimeter of ring 22 is locked in place and maintained.

In an embodiment of the present invention, following initial implantation and adjustment of the perimeter of ring 22, the perimeter of ring 22 may be later adjusted by a tool which lifts the lever arm of motion restrictor 60 such that recess-engaging portion 32 is no longer disposed within recess 29 and, thereby locking mechanism 43 is unlocked. Once recess 29 is free of recess-engaging portion 32, a portion of strip 28 adjacent to first end 51 thereof is allowed to slide with respect to housing 30. In some embodiments, a string is permanently coupled to recess-engaging portion 32 or to the lever arm of motion restrictor 60. Following initial implantation and adjustment of ring 22, a portion of the string is accessible from outside of ring 22, and by pulling on the string, the lever arm of motion restrictor 60 is lifted, thereby unlocking locking mechanism 43 by lifting recess-engaging portion 32 away from recess 29.

Figure 6:
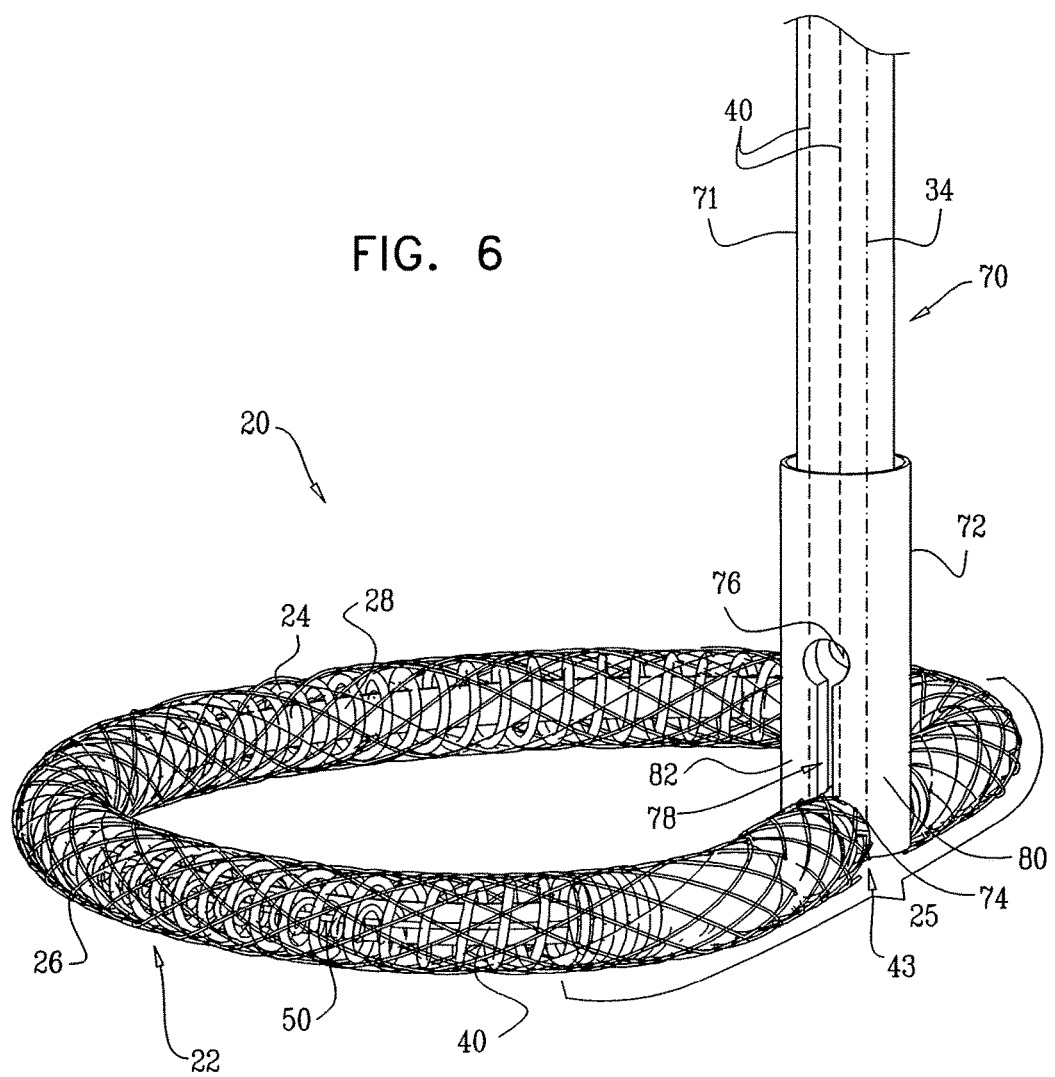
FIG. 6 is a schematic illustration of the annuloplasty ring structure of FIG. 1 being coupled to a delivery tool, in accordance with some embodiments of the present invention.

Reference is now made to FIG. 6, which is a schematic illustration of structure 20, in which ring 22 is removably coupled to a delivery tool 70, in accordance with some embodiments of the present invention. Delivery tool 70 is shaped to provide a body portion 71 having a lumen for slidable advancement therethrough of the first and second portions of flexible member 40 and of mechanical support 34. Respective ends of flexible member 40 and of mechanical support 34 are accessible from a proximal end of tool 70, i.e., the handle portion of tool 70. In some embodiments, the ends of flexible member 40 and of mechanical support 34 are exposed at the proximal end of tool 70. In some embodiments, respective ends of flexible member 40 and of mechanical support 34 are coupled to mechanical manipulators, e.g., knobs and gears, at the proximal end of tool 70.

The mechanical manipulators facilitate the pulling and/or relaxing of flexible member 40 and of mechanical support 34.

A distal portion of the body portion of tool 70 is coupled to a grasper tube 72. Grasper tube 72 comprises a flexible resilient material, e.g., nitinol. Grasper tube 72 is shaped to define respective slits 78 on opposing surfaces of tube 72 which run in parallel with a longitudinal axis of tool 70, and perpendicular with respect to a plane of ring 22 coupled to tool 70. Both slits 78 on the opposing surfaces of grasper tube 72 define first and second opposing distal portions 80 and 82 of tube 72. Each of first and second distal portions 80 and 82 of tube 72 is shaped to define a curved distal surface 74 which comes in contact with an external surface of housing 30 of locking mechanism 43. It is to be noted, however, that tube 72 may be coupled to any portion along ring 22. Curved surfaces 74 are shaped such that they cup housing 30 at respective surface thereof. Tube 72 is shown in a resting state thereof in which surfaces 74 cup housing 30 of locking mechanism 43 and the distal opposing portions 80 and 82 of tube 72 are aligned along the longitudinal axis of tool 70.

During decoupling of tool 70 from structure 20, the physician pulls on tool 70 such that surfaces 74 of portions 80 and 82 slide along the external convex surfaces provided by housing 30 and are thereby pushed radially away from housing 30. In other words, during decoupling of tool 70, the distal opposing portions are pushed angularly away from the longitudinal axis of tool 70 as tool 70 is pulled proximally away from ring 22. In response to the radial expanding of the distal portions of tube 72, tool 70 is decoupled from ring 22.

Tube 72 is shaped to define respective openings 76 at the proximal end of slits 78. Openings 76 facilitate radial angular displacement and expansion of the first and second distal portions 80 and 82 of tube 72.

The length and flexibility of tool 70 depends on the procedure used to implant ring 22 along the annulus. For embodiments in which ring 22 is positioned using open-heart or minimally-invasive procedures, the delivery tool may be shorter and more rigid than a delivery tool used to facilitate advancement and implantation of ring 22 in transcatheter procedures.

Following the adjustment of structure 20 and the contraction of the valve annulus, tool 70 is removed and flexible member 40 is pulled from within the lumen of inner body portion 50 and away from ring 22 leaving ring 22 implanted along the annulus and independent of flexible member 40.

For some applications, distal portions 80 and 82 are radially-expandable. During delivery of structure 20 toward the native heart valve, distal portions 80 and 82 are disposed within a slidable overtube that compresses distal portions 80 and 82. Following the adjustment of structure 20 and the contraction of the valve annulus, the overtube is slid proximally to expose distal portions 80 and 82. Responsively, distal portions 80 and 82 expand radially, and thereby decouple tool 70 from structure 20.

It is to be noted that housing 30 of locking mechanism 43 is shown in a vicinity of less-compressible portion 25 by way of illustration and not limitation. For example, housing 30 of locking mechanism 43 may be coupled to ring 22 along any suitable location thereof, e.g., in a vicinity of compressible portion 24 of outer body portion 55. For embodiments in which housing 30 is coupled to ring 22 in a vicinity of compressible portion 24 of outer body portion 55, following implantation of ring 22, housing 30 will be disposed with respect to the annulus of the patient along a portion thereof that is not between the trigones.

Reference is now made to FIGS. 1-6. Systems and annuloplasty structures described herein may be use in surgical procedures such as open-heart, minimally-invasive, or transcatheter procedures. For embodiments in which the annuloplasty structure is advanced toward the annulus in a transcatheter procedure, the annuloplasty structure may be folded, or otherwise compressed within a catheter used to advance the annuloplasty structure toward the valve. During open-heart, minimally-invasive, or transcatheter procedures, prior to advancement of the annuloplasty structure to the annulus, a plurality of sutures are sutured (e.g., during open-heart procedures), anchored, or otherwise coupled to the annulus. The sutures are then threaded through portions of the annuloplasty structure and facilitate advancement of the annuloplasty structure along the sutures and toward the annulus. Once positioned on the annulus, the sutures are locked in place, e.g., by a bead or by being tied, with respect to the annuloplasty structure, thereby locking in place the annuloplasty structure with respect to the annulus. For embodiments in which the annuloplasty structure is coupled to the annulus during an open-heart procedure, the structure may be first positioned along the annulus prior to being anchored thereto, e.g., by suturing the structure to the annulus, or by advancing anchors with respect to the structure and into tissue of the annulus.

Reference is again made to FIGS. 1-6. It is to be noted that, in some embodiments, ring 22 does not comprise less-compressible portion 25. For example, ring 22 may comprise only compressible material as described hereinabove with reference to FIG. 1 with respect to compressible portion 24.

Reference is yet again made to FIGS. 1-6. It is to be noted that strip 28 is used by way of illustration and not limitation. Alternatively to a strip, a tubular longitudinal element may be used and is shaped to provide a plurality of recesses that are engageable by locking mechanism 43.

Reference is again made to FIGS. 1-6. It is to be noted that inner body portion 50 is shown as comprising an elongate coil by way of illustration and not limitation. Alternatively, a plurality of short distinct tubular elements may be welded or otherwise coupled at respective portions thereof to outer surface 41 of strip 28, and each tubular element is shaped so as to provide a lumen for passage therethrough of flexible member 40. Further alternatively, a plurality of rings may be welded to the outer surface of strip 28 and function as a guide to support flexible member 40 at outer surface 41 of strip 28. It is to be noted that inner body portion 50 may be shaped to define any suitable shape in cross-section, e.g., circular, rectangular, square, oval, elliptical, triangular, semi-circular, partially-elliptical.

It is to be further noted that systems described herein for treatment of dilated mitral valves may be used to treat valves other than the mitral valve, mutatis mutandis. For example, structure 20 may be used to treat an aortic valve, a pulmonary valve, or a tricuspid valve of the patient. In some embodiments, systems described herein for use with a dilated annulus may be applied in order to treat dilated venous valves.

It is to be still further noted that systems described herein for treatment of mitral valves may be used to treat other annular muscles within the body of the patient. For example, the systems described herein may be used in order to treat a sphincter muscle within a stomach of the patient.

The techniques described herein may be performed in combination with techniques described in U.S. patent application Ser. No. 11/950,930 to Gross et al., filed Dec. 5, 2007, entitled, "Segmented ring placement," which issued as U.S.

Pat. No. 8,926,695, and which is assigned to the assignee of the present patent application and is incorporated herein by reference.

Additionally, techniques described herein may be performed in combination with techniques described in one or more of the following patent application, all of which are incorporated herein by reference:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007, which published as WO 08/068756;

U.S. patent application Ser. No. 11/950,930 to Gross at al., entitled, "Segmented ring placement," filed on Dec. 5, 2007, which published as US Patent Application Publication 2008/0262609, and which issued as U.S. Pat. No. 8,926,695;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008, which issued as U.S. Pat. No. 8,241,351;

U.S. Provisional Patent Application 61/207,908 to Miller et al., entitled, "Actively-engageable movement-restriction mechanism for use with an annuloplasty structure," filed on Feb. 17, 2009;

U.S. patent application Ser. No. 12/435,291 to Maisano et al., entitled, "Adjustable repair chords and spool mechanism therefor," filed on May 4, 2009, which issued as U.S. Pat. No. 8,147,542;

U.S. patent application Ser. No. 12/437,103 to Zipory et al., entitled, "Annuloplasty ring with intra-ring anchoring," filed on May 7, 2009, which issued as U.S. Pat. No. 8,715,342;

PCT Patent Application PCT/IL2009/000593 to Gross et al., entitled, "Annuloplasty devices and methods of delivery therefor," filed on Jun. 15, 2009, which published as WO 10/004546;

U.S. patent application Ser. No. 12/548,991 to Maisano et al., entitled, "Implantation of repair chords in the heart," filed on Aug. 27, 2009, which published as U.S. Pat. No. 8,808,368;

U.S. patent application Ser. No. 12/608,316 to Miller et al., entitled, "Tissue anchor for annuloplasty ring," filed on Oct. 29, 2009, which issued as U.S. Pat. No. 8,277,502;

U.S. Provisional Patent Application 61/265,936 to Miller et al., entitled, "Delivery tool for implantation of spool assembly coupled to a helical anchor," filed Dec. 2, 2009;

PCT Patent Application PCT/IL2009/001209 to Cabiri et al., entitled, "Adjustable annuloplasty devices and mechanisms therefor," filed on Dec. 22, 2009, which published as WO 10/073246;

U.S. patent application Ser. No. 12/689,635 to Zipory et al., entitled, "Over-wire rotation tool," filed on Jan. 19, 2010, which issued as U.S. Pat. No. 8,545,553; and/or U.S. patent application Ser. No. 12/689,693 to Hammer et al., entitled,"Application Deployment techniques for annuloplasty ring," filed on Jan. 19, 2010, which issued as U.S. Pat. No. 8,911,494.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
   an implant comprising:
      a flexible longitudinal member extending along a longitudinal length of the implant; and
      a flexible contracting member extending alongside the longitudinal member and along the longitudinal length of the implant, the contracting member being configured to facilitate reduction of a perimeter of the implant by applying a contracting force to the longitudinal member in response to an application of force to the contracting member, the longitudinal member having first and second ends, the first end being movable with respect to the second end responsively to the applying of the contracting force to the longitudinal member by the contracting member; and
      a lock coupled to the longitudinal member, the lock being engageable with the longitudinal member to restrict movement of the longitudinal member.

2. The apparatus according to claim 1, wherein the contracting member is moveable with respect to the longitudinal member while the longitudinal member is locked by the lock.

3. The apparatus according to claim 1, wherein the implant comprises a primary body portion having a lumen, and wherein the contracting member and the longitudinal member are disposed within the lumen.

4. The apparatus according to claim 1, wherein the implant comprises an annuloplasty ring.

5. The apparatus according to claim 1, wherein the lock is configured such that, while the lock is disengaged from the longitudinal member, a portion of the longitudinal member is movable bidirectionally with respect to the lock.

6. The apparatus according to claim 1, wherein the contracting member is disposed at a radially outer perimeter of the longitudinal member and is configured to apply a pushing force to the longitudinal member responsively to the application of the force to the contracting member.

7. The apparatus according to claim 6, wherein the implant comprises a body portion coupled to a radially outer surface of the longitudinal member, the body portion housing the contracting member and being configured to maintain the contracting member at the radially outer surface of the longitudinal member during the application of the force to the contracting member.

8. Apparatus, comprising:
   an implant comprising:

a flexible longitudinal member extending along a longitudinal length of the implant; and a flexible contracting member extending alongside the longitudinal member and along the longitudinal length of the implant; and a lock coupled to the longitudinal member, the lock being directly engageable with the longitudinal member to restrict movement of the longitudinal member with respect to the lock, wherein the lock is configured such that, while the lock is disengaged from the longitudinal member, the contracting member is configured to, in response to an application of force to the contracting member, reduce a perimeter of the implant and move a portion of the longitudinal member past the lock.

9. The apparatus according to claim 8, wherein the contracting member is moveable with respect to the longitudinal member while the longitudinal member is locked by the lock.

10. The apparatus according to claim 8, wherein the implant comprises a primary body portion having a lumen, and wherein the contracting member and the longitudinal member are disposed within the lumen.

11. The apparatus according to claim 8, wherein the implant comprises an annuloplasty ring.

12. The apparatus according to claim 8, wherein the lock is configured such that, while the lock is disengaged from the longitudinal member, the portion of the longitudinal member is movable bidirectionally with respect to the lock.

13. The apparatus according to claim 8, wherein the contracting member is disposed at a radially outer perimeter of the longitudinal member and is configured to apply a pushing force to the longitudinal member responsively to the application of the force to the contracting member.

14. The apparatus according to claim 13, wherein the implant comprises a body portion coupled to a radially outer surface of the longitudinal member, the body portion housing the contracting member and maintaining the contracting member at the radially outer surface of the longitudinal member during the application of the force to the contracting member.

15. A method, comprising:
advancing into a heart of a patient an implant including:
a flexible longitudinal member extending along a longitudinal length of the implant, and
a flexible contracting member extending alongside the longitudinal member and along the longitudinal length of the implant, the contracting member being configured to facilitate reduction of a perimeter of the longitudinal member by applying a contracting force to the longitudinal member in response to an application of force to the contracting member, the longitudinal member having first and second ends, the first end being movable with respect to the second end responsively to the applying of the contracting force to the longitudinal member by the contracting member, and
a lock coupled to the longitudinal member, the lock being engageable with a portion of the longitudinal member to restrict movement of the longitudinal member, contracting the longitudinal member by applying the force to the contracting member and thereby:

applying the contracting force to the longitudinal member by the contracting member; and moving the first end of the longitudinal member with respect to the second end of the longitudinal member; and subsequently to the contracting, locking the longitudinal member by the lock.

16. The method according to claim 15, further comprising, subsequently to the locking, moving the contracting member with respect to the longitudinal member.

17. Apparatus, comprising:
an implant comprising:
a flexible longitudinal member extending along a longitudinal length of the implant; and
a flexible contracting member extending alongside the longitudinal member and along the longitudinal length of the implant;
a primary body portion having a lumen, the contracting member and the longitudinal member being disposed within the lumen; and
a lock coupled to the longitudinal member, the lock being engageable with the longitudinal member to restrict movement of the longitudinal member with respect to the lock,
wherein the lock is configured such that, while the lock is disengaged from the longitudinal member, the contracting member is configured to, in response to an application of force to the contracting member, reduce a perimeter of the implant and move a portion of the longitudinal member past the lock.

18. Apparatus, comprising:
an implant comprising:
a flexible longitudinal member extending along a longitudinal length of the implant; and
a flexible contracting member extending alongside the longitudinal member and along the longitudinal length of the implant, the contracting member being disposed at a radially outer perimeter of the longitudinal member and configured to apply a pushing force to the longitudinal member responsively to the application of the force to the contracting member; and
a lock coupled to the longitudinal member, the lock being engageable with the longitudinal member to restrict movement of the longitudinal member with respect to the lock,
wherein the lock is configured such that, while the lock is disengaged from the longitudinal member, the contracting member is configured to, in response to an application of force to the contracting member, reduce a perimeter of the implant and move a portion of the longitudinal member past the lock.

\* \* \* \* \*